US006416753B1

(12) United States Patent
Yuan et al.

(10) Patent No.: US 6,416,753 B1
(45) Date of Patent: Jul. 9, 2002

(54) METHOD FOR MODULATING APOPTOSIS

(75) Inventors: Junying Yuan, Newton; Robert Friedlander, Cambridge, both of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 08/816,075

(22) Filed: Mar. 13, 1997

Related U.S. Application Data

(60) Provisional application No. 60/013,524, filed on Mar. 15, 1996.

(51) Int. Cl.[7] .................. A61K 45/00; A61K 39/395
(52) U.S. Cl. ................ 424/85.2; 424/144.1; 424/145.1
(58) Field of Search ................. 424/856, 85.2, 424/144.1, 145.1; 514/44, 2

(56) References Cited

U.S. PATENT DOCUMENTS

| | | | | |
|---|---|---|---|---|
| 5,135,917 A | * | 8/1992 | Bursch | 514/44 |
| 5,360,893 A | | 11/1994 | Owens et al. | 530/350 |
| 5,416,013 A | | 5/1995 | Black et al. | 435/226 |
| 5,508,262 A | * | 4/1996 | Norman et al. | 514/8 |
| 5,552,536 A | * | 9/1996 | Nicholson et al. | 536/23.1 |
| 5,585,357 A | | 12/1996 | Dolle et al. | 514/18 |
| 5,849,290 A | | 12/1998 | Brown et al. | 424/94.4 |

FOREIGN PATENT DOCUMENTS

| | | |
|---|---|---|
| WO | WO 93/05071 | 3/1993 |
| WO | WO 95/27792 | * 10/1995 |
| WO | WO 96/03982 | 2/1996 |

OTHER PUBLICATIONS

Sims et al. 1993. Proc. Natl. Acad. Sci. USA 90:6155–6159.*

Hogquist, et al. Proc. Natl. Acad. Sci. USA vol. 88(19): pp. 8485–8489, Oct. 1991.*

Kaneto, et al. Diabetes vol. 44: pp. 733–738, Jul. 1995.*

Schwartz et al. (1996) Binding sites and molecular mechanism of action of non–peptide ligands for peptide 7TM receptors. In "Structure and Function of 7TM Receptors" Schwartz et al. (Eds.) Munksgaard , Copenhagen. pp. 268–278.*

Dinarello, C.A., "Interleukin–1$^a$," *Ann N.Y. Acad. Sci.* 546:122–132 (1988).

Friendlander, R. et al., "Functional Role Of IL–1β In Apoptosis Mediated By The Ice Family," *CSH Abstract 1995*, p. 54 (1995).

Friedlander, R. et al., "Functional role of Interleukin 1β (IL–1β) in IL–1β–converting Enzyme–mediated Apoptosis," *J. Exp. Med.* 184:717–724 (Aug. 1996).

Pigott, R. and Davies, A.M., "The monoclonal antibody 69A1 recognizes an epitope found on neurones with axons that fasciculate but not on those with non–fasciculating processes," *Development* 100(3):489–500 (1987).

Revesz, L. et al., "Synthesis of P1 Aspartate–Based Peptide Acyloxymethyl and Fluoromethyl Ketones as Inhibitors of Interleukin–1 β–converting Enzyme," *Tetrahedron Lett.* 35:9693–9696 (1994).

Sarih, M., et al., "Silica induces apoptosis in macrophages and the release of interleukin–1α and interleukin–1β," *J. Leukoc. Biol.* 54(3):407–413 (1993).

Svoboda, K. and O'Shea, K., "An analysis of cell shape and the neuroepithelial basal lamina during optic vesicle formation in the mouse embryo," *Development* 100(2):185–200 (1987).

Zychlinsky, A., et al., "Interleukin–1 is released by Murine Macrophages during Apoptosis Induced by *Shigella flexneri*," *J. Clin. Invest.* 94(3):1328–1332 (1994).

Alcami, A. and G.L. Smith, "A Soluble Receptor for Interleukin–1β Encoded by Vaccinia Virus: A Novel Mechanism of Virus Modulation of the Host Response to Infection," *Cell* 71:153–167 (1992).

Ankarcrona, M. et al., "Interleukin–1β–Induced Nitric Oxide Production Activates Apoptosis in Pancreatic RINm5F Cells," *Exp. Cell Res.* 213:172–177 (1994).

Barr, P.J. and L.D. Tomei, "Apoptosis and Its Role in Human Disease," *Bio/Technol.* 12:487–493 (1994).

Belizario, J.E. and C.A. Dinarello, "Interleukin 1, Interleukin 6, Tumor Necrosis Factor, and Transforming Growth Factor β Increase Cell Resistance to Tumor Necrosis Factor Cytotoxicity by Growth Arrest in the $G_1$ Phase of the Cell Cycle," *Cancer Res.* 51:2379–2385 (1991).

Black, R.A. et al., "Activation of interleukin–1β by a co–induced protease," *FEBS Letters* 247:386–390 (1989).

Boudreau, N. et al., "Suppression of ICE and Apoptosis in Mammary Epithelial Cells by Extracellular Matrix," *Science* 267:891–893 (Feb. 1995).

Buttini, M. et al., "Induction of interleukin–1β mRNA after focal cerebral ischaemia in the rat," *Mol. Brain Res.* 23:126–134 (1994).

Casciola–Rosen, L.A. et al., "Specific Cleavage of the 70–kDa Protein Component of the U1 Small Nuclear Ribonucleoprotein Is a Characteristic Biochemical Feature of Apoptotic Cell Death," *J. Biol. Chem.* 269:30757–30760 (1994).

(List continued on next page.)

Primary Examiner—Karen Cochrane Carlson
(74) Attorney, Agent, or Firm—Sterne, Kessler, Goldstein & Fox P.L.L.C.

(57) ABSTRACT

Methods for modulating programmed cell death are provided. Apoptosis, induced by a variety of stimuli, can be inhibited by blocking IL–1β binding to its type–1 receptor. Additionally, IL–1β had anti-apoptotic activity when added exogenously prior to exposure to apoptotic stimuli. ICE cleavage of pro–IL–1β is an important step in apoptosis, and mature IL–1β may function as a positive or negative mediator of cell death.

9 Claims, 12 Drawing Sheets

OTHER PUBLICATIONS

Cerretti, D.P. et al., "Molecular Cloning of the Interleukin–1β Converting Enzyme," *Science* 256:97–100 (1992).

Chiarugi, V. et al., "Apoptosis and the Cell Cycle," *Cell. Mol. Biol. Res.* 40:603–612 (1994).

Chun, S.–Y. et al., "Interleukin–1β Suppresses Apoptosis in Rat Ovarian Follicles by Increasing Nitric Oxide Production," *Endocrinol.* 136:3120–3127 (Jul. 1995).

Cohen, J.J. and R.C. Duke, "Glucocorticoid Activation of a Calcium–Dependent Endonuclease in Thymocyte Nuclei Leads to Cell Death," *J. Immunol.* 132:38–42 (1984).

Davies, A.M., "Molecular and cellular aspects of patterning sensory neurone connections in the vertebrate nervous system," *Development* 101:185–208 (1987).

di Giovine, F.S. and G.W. Duff, "Interleukin 1: the first interleukin," *Immunol. Today* 11:13–20 (1990).

Dinarello, C.A., "Interleukin–1 and Interleukin–1 Antagonism," *Blood* 77:1627–1652 (1991).

Dinarello, C.A., "The interleukin–1 family: 10 years of discovery," *FASEB J.* 8:1314–1325 (1994).

Dripps, D.J. et al., "Interleukin–1 (IL–1) Receptor Antagonist Binds to the 80–kDa IL–1 Receptor but Does Not Initiate IL–1 Signal Transduction," *J. Biol. Chem.* 266:10331–10336 (1991).

Ellis, R.E. and H.R. Horvitz, "Two *C. elegans* genes control the programmed deaths of specific cells in the pharynx," *Develop.* 112:591–603 (1991).

Ellis, R.E. et al., "Mechanisms and Functions of Cell Death," *Annu. Rev. Cell Biol.* 7:663–698 (1991).

Enari, M. et al., "Involvement of an ICE–like protease in Fas–mediated apoptosis," *Nature* 375:78–81 (May 1995).

Englemann, H. et al., "Antibodies to a Soluble Form of a Tumor Necrosis Factor (TNF) Receptor Have TNF–like Activity," *J. Biol. Chem.* 265:14497–14504 (1990).

Estrov, Z. et al., "Effect of Interleukin–1β Converting Enzyme Inhibitor on Acute Myelogenous Leukemia Progenitor Proliferation," *Blood* 86:4594–4602 (Dec. 1995).

Fernandes–Alnemri, T. et al., "CPP32, a Novel Human Apoptotic Protein with Homology to *Caenorhabditis elegans* Cell Death Protein Ced–3 and Mammalian Interleukin–1β–converting Enzyme," *J. Biol. Chem.* 269:30761–30764 (1994).

Fernandes–Alnemri, T. et al., "Mch2, a New Member of the Apoptotic *Ced–3/Ice* Cysteine Protease Gene Family," *Cancer Res.* 55:2737–2742 (Jul. 1995).

Fratelli, M. et al., "Autocrine Interleukin–1β Regulates Both Proliferation and Apoptosis in EL4–6.1 Thymoma Cells," *Blood* 85:3532–3537 (Jun. 1995).

Freidin, M. et al., "Cultured sympathetic neurons synthesize and release the cytokine interleukin 1β," *Proc. Natl. Acad. Sci. USA* 89:10440–10443 (1992).

Friedlander, R.M. et al., "Functional Role of Interleukin 1β(IL–1β) in IL–1β–converting Enzyme–mediated Apoptosis," *J. Exp. Med.* 184:717–724 (Aug. 1996).

Furukawa, Y. et al., "Preferential Production of Interleukin–1β over Interleukin–1 Receptor Antagonist Contributes to Proliferation and Suppression of Apoptosis in Leukemic Cells," *Jpn. J. Cancer Res.* 86:208–216 (Feb. 1995).

Gagliardini, V. et al., "Prevention of Vertebrate Neuronal Death by the crmA Gene," *Science* 263:826–828 (1994).

Glücksmann, A., "Cell Deaths in Normal Vertebrate Ontogeny," *In: Biol. Rev. of the Cambridge Philos. Soc.*, vol. 26, Fox, H.M. ed., Cambridge Univ. Press, publ., pp. 59–86 (1951).

Graeber, T.G. et al., "Hypoxia–mediated selection of cells with diminished apoptotic potential in solid tumours," *Nature* 379:88–91 (Jan. 1996).

Granowitz, E.V. et al., "Interleukin–1 Receptor Antagonist Competitively Inhibits the Binding of Interleukin–1 to the Type II Interleukin–1 Receptor," *J. Biol. Chem.* 266:14147–14150 (1991).

Griffin, W.S.T. et al., "Brain interleukin 1 and S–100 immunoreactivity are elevated in Down syndrome and Alzheimer disease," *Proc. Natl. Acad. Sci. USA* 86:7611–7615 (1989).

Guo, K.Y. et al., "Apoptosis of AMLs Induced by IL–1 RAP," *Blood* 86(*Suppl. 1*):695A, Abstract No. 2767 (Nov. 1995).

Haimovitz–Friedman, A. et al., "Ionizing Radiation Acts on Cellular Membranes to Generate Ceramide and Initiate Apoptosis," *J. Exp. Med.* 180:525–535 (1994).

Hsu, H. et al., "The TNF Receptor 1–Associated Protein TRADD Signals Cell Death and NF–κB Activation," *Cell* 81:495–504 (May 1995).

Jacobson, M.D. and M.C. Raff,"Programmed cell death and Bcl–2 protection in very low oxygen," *Nature* 374:814–816 (Apr. 1995).

Kamens, J. et al., "Identification and Characterization of ICH–2, a Novel Member of the Interleukin–1β–converting Enzyme Family of Cysteine Proteases," *J. Biol. Chem.* 270:15250–15256 (Jun. 1995).

Karp, J.E. and S. Broder, "New Directions in Molecular Medicine," *Cancer Res.* 54:653–665 (1994).

Kostura, M.J. et al., "Identification of a monocyte specific pre–interleukin 1β convertase activity," *Proc. Natl. Acad. Sci. USA* 86:5227–5231 (1989).

Kuida, K. et al., "Altered Cytokine Export and Apoptosis in Mice Deficient in Interleukin–1β Converting Enzyme," *Science* 267:2000–2003 (Mar. 1995).

Kumar, S. et al., "Induction of apoptosis by the mouse Nedd2 gene, which encodes a protein similar to the product of the *Caenorhabditis elegans* cell death gene ced–3 and the mammalian Il–1β –converting enzyme," *Genes & Develop.* 8:1613–1626 (1994).

Laster, S.M. et al., "Tumor Necrosis Factor can Induce both Apoptic and Necrotic Forms of Cell Lysis," *J. Immunol.* 141:2629–2634 (1988).

Lazebnik, Y.A. et al., "Cleavage of poly(ADP–ribose) polymerase by a proteinase with properties like ICE," *Nature* 371:346–347 (1994).

Lazebnik, Y.A. et al., "Studies of the lamin protease reveal multiple parallel biochemical pathways during apoptotic execution," *Proc. Natl. Acad. Sci. USA* 92:9042–9046 (Sep. 1995).

Li, P. et al., "Mice Deficient in IL–1β–Converting Enzyme Are Defective in Production of Mature IL–1β and Resistant to Endotoxic Shock," *Cell* 80:401–411 (Feb. 1995).

Liu, T. et al., "Interleukin–1β mRNA Expression in Ischemic Rat Cortex," *Stroke* 24:1746–1751 (1993).

Los, M. et al., "Requirement of an ICE/CED–3 protease for Fas/APO–1–mediated apoptosis," *Nature* 375:81–83 (May 1995).

Martin, D.P. et al., "Inhibitors of Protein Synthesis and RNA Synthesis Prevent Neuronal Death Caused by Nerve Growth Factor Deprivation," *J. Cell Biol.* 106:829–844 (1988).

Mathias, S. et al., "Activation of the Sphingomyelin Signaling Pathway in Intact EL4 Cells and in a Cell–Free System by IL–1β," *Science* 259:519–522 (1993).

Meikrantz, W. et al., "Activation of cyclin A–dependent protein kinases during apoptosis," *Proc. Natl. Acad. Sci. USA* 91:3754–3758 (1994).

Miura, M. et al., "Induction of Apoptosis in Fibroblasts by IL–1β–Converting Enzyme, a Mammalian Homolog of the *C. elegans* Cell Death Gene ced–3," *Cell* 75:653–660 (1993).

Miura, M. et al., "Tumor necrosis factor–induced apoptosis is mediated by a CrmA–sensitive cell death pathway," *Proc. Natl. Acad. Sci. USA* 92:8318–8322 (Aug. 1995).

Munday, N.A. et al., "Molecular Cloning and Pro–apoptotic Activity of $ICE_{rel}II$ and $ICE_{rel}III$, Members of the ICE/CED–3 Family of Cysteine Proteases," *J. Biol. Chem.* 270:15870–15876 (Jun. 1995).

Nicholson, D.W. et al., "Identification and inhibition of the ICE/CED–3 protease necessary for mammalian apoptosis," *Nature* 376:37–43 (Jul. 1995).

Onozaki, K. et al., "Human Interleukin 1 is a Cytocidal Factor for Several Tumor Cell Lines," *J. Immunol.* 135:3962–3967 (1985).

Palumbo, G.J. et al., "Inhibition of an Inflammatory Response Is Mediated by a 38–kDa Protein of Cowpox Virus," *Virol.* 172:262–273 (1989).

Pigott, R. and A.M. Davies, "The monoclonal antibody 69A1 recognizes an epitope found on neurones with axons that fasciculate but not on those with non–fasciculating processes," *Development* 100:489–500 (1987).

Raingeaud, J. et al., "Pro–inflammatory Cytokines and Environmental Stress Cause p38 Mitogen–activated Protein Kinase Activation by Dual Phosphorylation on Tyrosine and Threonine," *J. Biol. Chem.* 270:7420–7426 (Mar. 1995).

Ray, C.A. et al., "Viral Inhibition of Inflammatory: Cowpox Virus Encodes an Inhibitor of the Interleukin–1β Converting Enzyme," *Cell* 69:597–604 (1992).

Relton, J.K. and N.J. Rothwell, "Interleukin–1 Receptor Antagonist Inhibits Ischaemic and Excitotoxic Neuronal Damage in the Rat," *Brain Res. Bull.* 29:243–246 (1992).

Rodriguez, C. et al., "Interleukin–1β Suppresses Apoptosis in CD34 Positive Bone Marrow Cells Through Activation of the Type I IL–1 Receptor," *J. Cell. Physiol.* 166:387–395 (Feb. 1996).

Shi, L. et al., "Activation of an interleukin 1 converting enzyme–dependent apoptosis pathway by granzyme B," *Proc. Natl. Acad. Sci. USA* 93:11002–11007 (Oct. 1996).

Shimizu, S. et al., "Prevention of hypoxia–induced cell death by Bcl–2 and Bcl–xL," *Nature* 374:811–813 (Apr. 1995).

Smith, C.A. et al., "A Receptor for Tumor Necrosis Factor Defines an Unusual Family of Cellular and Viral Proteins," *Science* 248:1019–1023 (1990).

Spriggs, M.K. et al., "Vaccinia and Cowpox Viruses Encode a Novel Secreted Interleukin–1–Binding Protein," *Cell* 71:145–152 (1992).

Stanisic, T. et al., "Partial Inhibition of Castration Induced Ventral Prostate Regression with Actinomycin D and Cycloheximide,"0 *Invest. Urology* 16:19–22 (1978).

Strijbos, P.J.L.M. and N.J. Rothwell, "Interleukin–1β Attenuates Excitatory Amino Acid–Induced Neurodegeneration in vitro:Involvement of Nerve Growth Factor," *J. Neurosci.* 15:3468–3474 (May 1995).

Tewari, M. and V.M. Dixit, "Fas– and Tumor Necrosis Factor–induced Apoptosis Is Inhibited by the Poxvirus crmA Gene Product," *J. Biol. Chem.* 270:3255–3260 (Feb. 1995).

Tewari, M. et al., "Yama/CPP32β, a Mammalian Homolog of CED–3, Is a CrmA–Inhibitable Protease That Cleaves the Death Substrate Poly(ADP–Ribose) Polymerase," *Cell* 81:801–809 (Jun. 1995).

Thoma, B. et al., "Identification of a 60–kD Tumor Necrosis Factor (TNF) Receptor as the Major Signal Transducing Component in TNF Responses," *J. Exp. Med.* 172:1019–1023 (1990).

Thornberry, N.A. et al., "A novel heterodimeric cysteine protease is required for interleukin–1β processing in monocytes," *Nature* 356:768–774 (1992).

Tracey, K.J. and A. Cerami, "Tumor Necrosis Factor, Other Cytokines and Disease," *Annu. Rev. Cell Biol.* 9:317–343 (1993).

Vaux, D.L. et al., "An Evolutionary Perspective on Apoptosis," *Cell* 76:777–779 (1994).

Wang, L. et al., "Ich–1, an Ice/ced–3–Related Gene, Encodes Both Positive and Negative Regulators of Programmed Cell Death," *Cell* 78:739–750 (1994).

White, E. et al., "The 19–Kilodalton Adenovirus E1B Transforming Protein Inhibits Programmed Cell Death and Prevents Cytolysis by Tumor Necrosis Factor α," *Mol. Cell. Biol.* 12:2570–2580 (1992).

Wyllie, A.H. et al., "Cell Death: The Significance of Apoptosis," *In: International Review of Cytology*, Bourne, G.H. and Danielli, J.F., eds., Academic Press, New York, Inc., publ., pp. 251–306 (1980).

Wyllie, A.H., "Cell death: a new classification separating apoptosis from necrosis," *In: Cell death in biology and pathology*, Bowen, I.D. and Lockshin, R.A., eds., Chapman and Hall, New York, publ., pp. 9–34 (1981).

Xia, Z. et al., "Opposing Effects of ERK and JNK–p38 MAP Kinases on Apoptosis," *Science* 270:1326–1331 (Nov. 1995).

Yuan, J. and H.R. Horvitz, "The *Caenorhabditis elegans* Genes ced–3 and ced–4 Act Cell Autonomously to Cause Programmed Cell Death," *Develop. Biol.* 138:33–41 (1990).

Yuan, J. et al., "The *C. elegans* Cell Death Gene ced–3 Encodes a Protein Similar to Mammalian Interleukin–1β–Converting Enzyme," *Cell* 75:641–652 (1993).

Zychlinsky, A. et al., "Interleukin 1 Is Released by Murine Macrophages during Apoptosis Induced by *Shigella flexneri*," *J. Clin. Invest.* 94:1328–1332 (1994).

International Search Report of International Application No. PCT/US96/03468, mailed Jan. 31, 1997.

\* cited by examiner

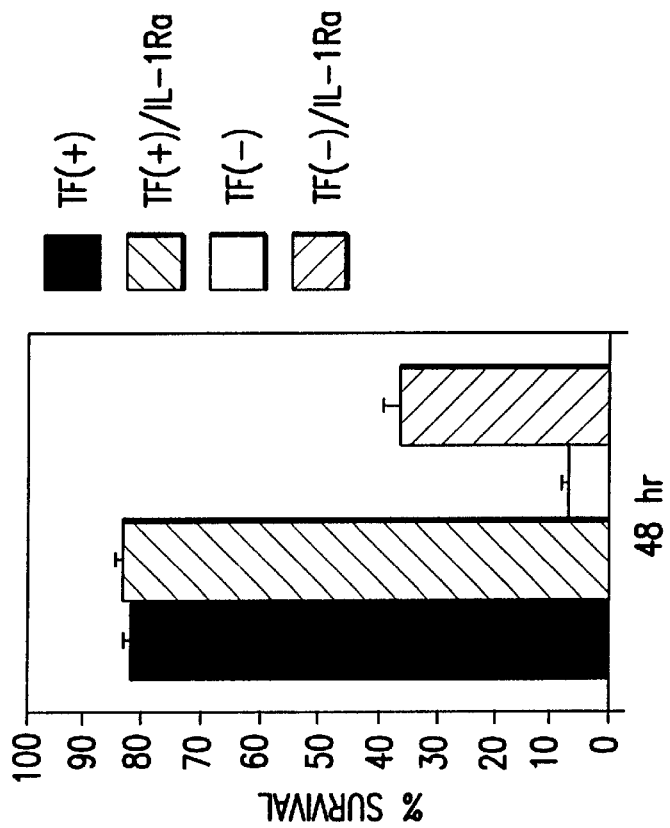
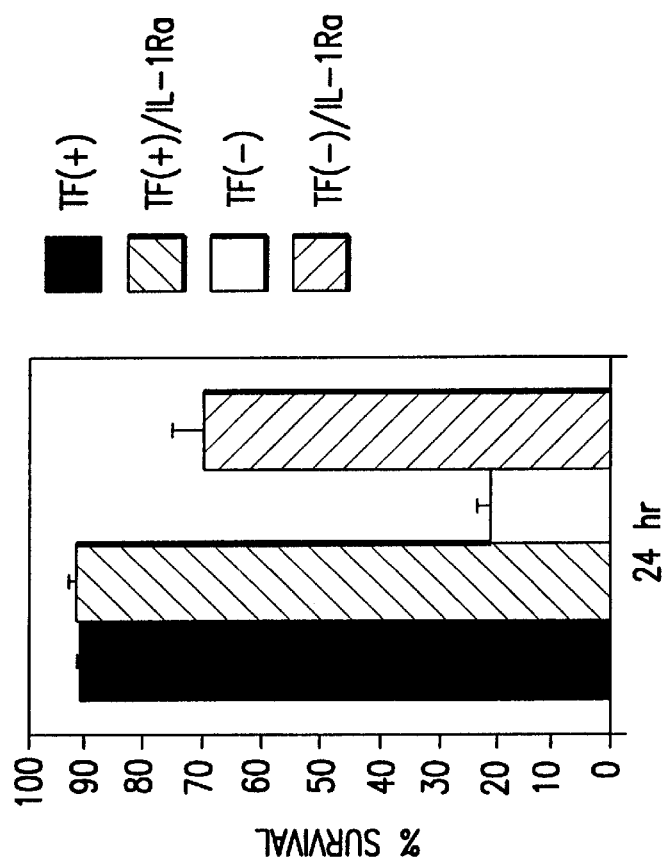

```
1    GCACAAGGAGCTGATGGCCGCTGACAGGGGACGCAGGATATTGGGAGTGTGTGGCATGCATCCTCATCATCAGGAAACTC
              M  A  A  D  R  G  R  R  I  L  G  V  C  G  M  H  P  H  H  Q  E  T  L

81   TAAAAAGAACCGAGTGGTGCTAGCCAAACAGCTGTTGTTGAGCGAATTGTTAGAACATCTTCTGGAAGGACATCATC
      K  K  N  R  V  V  L  A  K  Q  L  L  S  E  L  L  E  H  L  L  E  K  D  I  I

161  ACCTTGGAAATGAGGGAGCTCATCCAGGCCAAAGTGGGCAGTTTCAGCCAGAATGTGGAACTCCTCAACTTGCCTAA
      T  L  E  M  R  E  L  I  Q  A  K  V  G  S  F  S  Q  N  V  E  L  L  N  L  L  P  K

241  GAGGGGTCCCCAAGCTTTTGATGCCTTCTGTGAAGCACTGAGGGAGACCAAGCCACCTGGAGGATATGTTGCTCA
      R  G  P  Q  A  F  D  A  F  C  E  A  L  R  E  T  K  Q  G  H  L  E  D  M  L  L  T

321  CCACCCTTTCTGGGCTTCAGTACTCCCACCGTTGAGCTGTGTGAGTCTCCCTTTTCCGGTGTGTGAG
      T  L  S  G  L  Q  H  V  L  P  P  L  S  C  D  Y  D  L  S  L  P  F  P  V  C  E

401  TCCTGTCCCCTTTACAAGAAGCTCCGCTGTCCTGAATTTTATCAAACACACTTCCAGTGGCATATAGGTTGCAGTGTCCTGTCTG
      S  C  P  L  Y  K  K  L  R  L  S  T  D  T  V  E  H  S  L  D  N  K  D  G  P  V  C

481  CCTTCAGGTGAAGCCTTGCACTCCCTGAATTTTATCAAACACACTTCCAGTGGCATATAGGTTGCAGTCTCCGGCCTGTG
      L  Q  V  K  P  C  T  P  E  F  Y  Q  T  H  F  Q  L  A  Y  R  L  Q  S  R  P  R  G

561  GCCTAGCCACTGGTGTTGAGCAATGCACTTCACTGGAGAGAAAGAACTGGAATTTCGCTCTGGAGGGGATGTGGACCAC
      L  A  L  V  L  S  N  V  H  F  T  G  E  K  E  L  E  F  R  S  G  G  D  V  D  H
```

FIG. 7A

```
641  AGTACTCTAGTCACCCTCTTCAAGCTTTTGGGCTATGACGTCCATGTTCTATGTGACCAGACTGCACAGGAAATGCAAGA
     ---------+---------+---------+---------+---------+---------+---------+---------+
      S  T  L  V  T  L  F  K  L  L  G  Y  D  V  H  V  L  C  D  Q  T  A  Q  E  M  Q  E

721  GAAACTGCAGAATTTTGCACAGTTACCTGCACACCGAGTCACGGACTCCTGCATCGTGGCACTCCTCGCATGGTGTGG
     ---------+---------+---------+---------+---------+---------+---------+---------+
      K  L  Q  N  F  A  Q  L  P  A  H  R  V  T  D  S  C  I  V  A  L  L  S  H  G  V  E

801  AGGGCGCCATCTATGGTGTGGATGGGAAACTGCTCCAGCTCCAAGAGGTTTTTCAGCTCTTTGACAACGCCAACTGCCCA
     ---------+---------+---------+---------+---------+---------+---------+---------+
      G  A  I  Y  G  V  D  G  K  L  L  Q  L  Q  E  V  F  Q  L  F  D  N  A  N  C  P

881  AGCCTACAGAACAAACCAAAAATGTTCTTCATCCAGGCCTGCCGTGGAGATGAGACTGATCGTGGGGTTGACCAACAAGA
     ---------+---------+---------+---------+---------+---------+---------+---------+
      S  L  Q  N  K  P  K  M  F  F  I  Q  A  C  R  G  D  E  T  D  R  G  V  D  Q  Q  D

961  TGGAAAGAACCACGCCAGGATCCCCTGGGTGCGAGGAGAGTGATGCCGGTAAAGAAAAAGTTGCCGAAGATGAGACTGCCCA
     ---------+---------+---------+---------+---------+---------+---------+---------+
      G  K  N  H  A  G  S  P  G  C  E  E  S  D  A  G  K  E  K  L  P  K  M  R  L  P  T

1041 CGGCGCTCAGACATGATATGCGGCTATGCCTGTTTTCTGAGGCGGGCTTGTGATATGCACGTGGCCGACATGCTGGTTAAGGTGAACGCACT
     ---------+---------+---------+---------+---------+---------+---------+---------+
      R  S  D  M  I  C  G  Y  A  C  L  K  G  T  A  A  M  R  N  T  K  R  G  S  W  Y

1121 ATCGAGGCTCTTGCTCAAGTGTTTCTGAGCCGGGCTTGTGATATGCACGTGGCCGACATGCTGGTTAAGGTGAACGCACT
     ---------+---------+---------+---------+---------+---------+---------+---------+
      I  E  A  L  A  Q  V  F  S  E  R  A  C  D  M  H  V  A  D  M  L  V  K  V  N  A  L

1201 TATCAAGGATCGGGAAGGTTATGCTCCTGGCACAGAATTCCACCGGTGCAAGGAAATGTCTGAATACTGCAGCACTCTGT
     ---------+---------+---------+---------+---------+---------+---------+---------+
      I  K  D  R  E  G  Y  A  P  G  T  E  F  H  R  C  K  E  M  S  E  Y  C  S  T  L  C
```

FIG. 7B

```
1281  GCCGGCCACCTCTACCTGTTCCCAGGACACCCTCCCCACATGATGTCACCTCCCCATCATCCAGCCAAGTGGAAGCCACTG
       ---+---------+---------+---------+---------+---------+---------+---------+---------+
        R  H  L  Y  L  F  P  G  H  P  P  T  *
1361  GACCACAGGAGGTGTGATAGAGCCTTTGATCTTCAGGATGCACGGTTTCTGTTCTGCCCCTCAGGGATGTGGGAATCTC
       ---+---------+---------+---------+---------+---------+---------+---------+---------+
1441  CCAGACTTGTTTCCTG
       ---+---------+--
```

FIG. 7C

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 1456 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 14..1318

(xi) SEQUENCE DESCRIPTION: SEQ ID NO:1:

```
GCACAAGGAG CTG ATG GCC GCT GAC AGG GGA CGC A GG ATA TTG GGA GTG        49
            Met Ala Ala Asp Arg Gly Arg   Ile Leu Gly Val
            1           5                     10

TGT GGC ATG CAT CCT CAT CAT CAG GAA ACT C TA AAA AAG AAC CGA GTG        97
Cys Gly Met His Pro His His Gln Glu Thr L eu Lys Lys Asn Arg Val
            15                  20              25

GTG CTA GCC AAA CAG CTG TTG TTG AGC GAA T TG TTA GAA CAT CTT CTG       145
Val Leu Ala Lys Gln Leu Leu Leu Ser Glu L eu Leu Glu His Leu Leu
        30                  35                  40

GAG AAG GAC ATC ATC ACC TTG GAA ATG AGG G AG CTC ATC CAG GCC AAA       193
Glu Lys Asp Ile Ile Thr Leu Glu Met Arg G lu Leu Ile Gln Ala Lys
45                  50                  55                  60

GTG GGC AGT TTC AGC CAG AAT GTG GAA CTC C TC AAC TTG CTG CCT AAG       241
Val Gly Ser Phe Ser Gln Asn Val Glu Leu L eu Asn Leu Leu Pro Lys
                65                  70                  75

AGG GGT CCC CAA GCT TTT GAT GCC TTC TGT G AA GCA CTG AGG GAG ACC       289
Arg Gly Pro Gln Ala Phe Asp Ala Phe Cys G lu Ala Leu Arg Glu Thr
            80                  85                  90

AAG CAA GGC CAC CTG GAG GAT ATG TTG CTC A CC ACC CTT TCT GGG CTT       337
Lys Gln Gly His Leu Glu Asp Met Leu Leu T hr Thr Leu Ser Gly Leu
        95                  100                 105

CAG CAT GTA CTC CCA CCG TTG AGC TGT GAC T AC GAC TTG AGT CTC CCT       385
Gln His Val Leu Pro Pro Leu Ser Cys Asp T yr Asp Leu Ser Leu Pro
    110                 115                 120

TTT CCG GTG TGT GAG TCC TGT CCC CTT TAC A AG AAG CTC CGC CTG TCG       433
Phe Pro Val Cys Glu Ser Cys Pro Leu Tyr L ys Lys Leu Arg Leu Ser
125                 130                 135                 140

ACA GAT ACT GTG GAA CAC TCC CTA GAC AAT A AA GAT GGT CCT GTC TGC       481
Thr Asp Thr Val Glu His Ser Leu Asp Asn L ys Asp Gly Pro Val Cys
                145                 150                 155

CTT CAG GTG AAG CCT TGC ACT CCT GAA TTT T AT CAA ACA CAC TTC CAG       529
Leu Gln Val Lys Pro Cys Thr Pro Glu Phe T yr Gln Thr His Phe Gln
            160                 165                 170

CTG GCA TAT AGG TTG CAG TCT CGG CCT CGT G GC CTA GCA CTG GTG TTG       577
Leu Ala Tyr Arg Leu Gln Ser Arg Pro Arg G ly Leu Ala Leu Val Leu
        175                 180                 185

AGC AAT GTG CAC TTC ACT GGA GAG AAA GAA C TG GAA TTT CGC TCT GGA       625
Ser Asn Val His Phe Thr Gly Glu Lys Glu L eu Glu Phe Arg Ser Gly
    190                 195                 200

GGG GAT GTG GAC CAC AGT ACT CTA GTC ACC C TC TTC AAG CTT TTG GGC       673
Gly Asp Val Asp His Ser Thr Leu Val Thr L eu Phe Lys Leu Leu Gly
205                 210                 215                 220

TAT GAC GTC CAT GTT CTA TGT GAC CAG ACT G CA CAG GAA ATG CAA GAG       721
Tyr Asp Val His Val Leu Cys Asp Gln Thr A la Gln Glu Met Gln Glu
                225                 230                 235

AAA CTG CAG AAT TTT GCA CAG TTA CCT GCA C AC CGA GTC ACG GAC TCC       769
Lys Leu Gln Asn Phe Ala Gln Leu Pro Ala H is Arg Val Thr Asp Ser
            240                 245                 250

TGC ATC GTG GCA CTC CTC TCG CAT GGT GTG G AG GGC GCC ATC TAT GGT       817
Cys Ile Val Ala Leu Leu Ser His Gly Val G lu Gly Ala Ile Tyr Gly
        255                 260                 265

GTG GAT GGG AAA CTG CTC CAG CTC CAA GAG G TT TTT CAG CTC TTT GAC       865
Val Asp Gly Lys Leu Leu Gln Leu Gln Glu V al Phe Gln Leu Phe Asp
    270                 275                 280

AAC GCC AAC TGC CCA AGC CTA CAG AAC AAA C CA AAA ATG TTC TTC ATC       913
Asn Ala Asn Cys Pro Ser Leu Gln Asn Lys P ro Lys Met Phe Phe Ile
285                 290                 295                 300
```

```
CAG GCC TGC CGT GGA GAT GAG ACT GAT CGT G GG GTT GAC CAA CAA GAT       961
Gln Ala Cys Arg Gly Asp Glu Thr Asp Arg G ly Val Asp Gln Gln Asp
                    305                 310                 315

GGA AAG AAC CAC GCA GGA TCC CCT GGG TGC G AG GAG AGT GAT GCC GGT      1009
Gly Lys Asn His Ala Gly Ser Pro Gly Cys G lu Glu Ser Asp Ala Gly
                320                 325                 330

AAA GAA AAG TTG CCG AAG ATG AGA CTG CCC A CG CGC TCA GAC ATG ATA      1057
Lys Glu Lys Leu Pro Lys Met Arg Leu Pro T hr Arg Ser Asp Met Ile
            335                 340                 345

TGC GGC TAT GCC TGC CTC AAA GGG ACT GCC G CC ATG CGG AAC ACC AAA      1105
Cys Gly Tyr Ala Cys Leu Lys Gly Thr Ala A la Met Arg Asn Thr Lys
        350                 355                 360

CGA GGT TCC TGG TAC ATC GAG GCT CTT GCT C AA GTG TTT TCT GAG CGG      1153
Arg Gly Ser Trp Tyr Ile Glu Ala Leu Ala G ln Val Phe Ser Glu Arg
365                 370                 375                 380

GCT TGT GAT ATG CAC GTG GCC GAC ATG CTG G TT AAG GTG AAC GCA CTT      1201
Ala Cys Asp Met His Val Ala Asp Met Leu V al Lys Val Asn Ala Leu
                385                 390                 395

ATC AAG GAT CGG GAA GGT TAT GCT CCT GGC A CA GAA TTC CAC CGG TGC      1249
Ile Lys Asp Arg Glu Gly Tyr Ala Pro Gly T hr Glu Phe His Arg Cys
                400                 405                 410

AAG GAA ATG TCT GAA TAC TGC AGC ACT CTG T GC CGC CAC CTC TAC CTG      1297
Lys Glu Met Ser Glu Tyr Cys Ser Thr Leu C ys Arg His Leu Tyr Leu
            415                 420                 425

TTC CCA GGA CAC CCT CCC ACA TGATGTCACC TCCCCATC AT CCACGCCAAG         1348
Phe Pro Gly His Pro Pro Thr
            430             435

TGGAAGCCAC TGGACCACAG GAGGTGTGAT AGAGCCTTTG ATCTTCAGGA T GCACGGTTT    1408

CTGTTCTGCC CCCTCAGGGA TGTGGGAATC TCCCAGACTT GTTTCCTG                  1456

(2) INFORMATION FOR SEQ ID NO:2:

(i) SEQUENCE CHARACTERISTICS:
        (A) LENGTH: 435 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Ala Asp Arg Gly Arg Arg Ile Leu G ly Val Cys Gly Met His
1               5                   10                  15

Pro His His Gln Glu Thr Leu Lys Lys Asn A rg Val Val Leu Ala Lys
            20                  25                  30

Gln Leu Leu Leu Ser Glu Leu Leu Glu His L eu Leu Glu Lys Asp Ile
        35                  40                  45

Ile Thr Leu Glu Met Arg Glu Leu Ile Gln A la Lys Val Gly Ser Phe
    50                  55                  60

Ser Gln Asn Val Glu Leu Leu Asn Leu Leu P ro Lys Arg Gly Pro Gln
65              70                  75                  80

Ala Phe Asp Ala Phe Cys Glu Ala Leu Arg G lu Thr Lys Gln Gly His
            85                  90                  95

Leu Glu Asp Met Leu Leu Thr Thr Leu Ser G ly Leu Gln His Val Leu
            100                 105                 110

Pro Pro Leu Ser Cys Asp Tyr Asp Leu Ser L eu Pro Phe Pro Val Cys
        115                 120                 125
```

```
Glu Ser Cys Pro Leu Tyr Lys Lys Leu Arg Leu Ser Thr Asp Thr Val
    130             135             140

Glu His Ser Leu Asp Asn Lys Asp Gly Pro Val Cys Leu Gln Val Lys
145             150             155             160

Pro Cys Thr Pro Glu Phe Tyr Gln Thr His Phe Gln Leu Ala Tyr Arg
            165             170             175

Leu Gln Ser Arg Pro Arg Gly Leu Ala Leu Val Leu Ser Asn Val His
            180             185             190

Phe Thr Gly Glu Lys Glu Leu Glu Phe Arg Ser Gly Gly Asp Val Asp
            195             200             205

His Ser Thr Leu Val Thr Leu Phe Lys Leu Leu Gly Tyr Asp Val His
            210             215             220

Val Leu Cys Asp Gln Thr Ala Gln Glu Met Gln Glu Lys Leu Gln Asn
225             230             235             240

Phe Ala Gln Leu Pro Ala His Arg Val Thr Asp Ser Cys Ile Val Ala
            245             250             255

Leu Leu Ser His Gly Val Glu Gly Ala Ile Tyr Gly Val Asp Gly Lys
            260             265             270

Leu Leu Gln Leu Gln Glu Val Phe Gln Leu Phe Asp Asn Ala Asn Cys
            275             280             285

Pro Ser Leu Gln Asn Lys Pro Lys Met Phe Phe Ile Gln Ala Cys Arg
            290             295             300

Gly Asp Glu Thr Asp Arg Gly Val Asp Gln Gln Asp Gly Lys Asn His
305             310             315             320

Ala Gly Ser Pro Gly Cys Glu Glu Ser Asp Ala Gly Lys Glu Lys Leu
            325             330             335

Pro Lys Met Arg Leu Pro Thr Arg Ser Asp Met Ile Cys Gly Tyr Ala
            340             345             350

Cys Leu Lys Gly Thr Ala Ala Met Arg Asn Thr Lys Arg Gly Ser Trp
            355             360             365

Tyr Ile Glu Ala Leu Ala Gln Val Phe Ser Glu Arg Ala Cys Asp Met
    370             375             380

His Val Ala Asp Met Leu Val Lys Val Asn Ala Leu Ile Lys Asp Arg
385             390             395             400

Glu Gly Tyr Ala Pro Gly Thr Glu Phe His Arg Cys Lys Glu Met Ser
            405             410             415

Glu Tyr Cys Ser Thr Leu Cys Arg His Leu Tyr Leu Phe Pro Gly His
            420             425             430

Pro Pro Thr
    435

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:3:

Gln Ala Cys Arg Gly
1               5
```

METHOD FOR MODULATING APOPTOSIS

This application claims the benefit of the filing date of U.S. Provisional Application 60/013,524, filed Mar. 15, 1996 and is incorporated herein by reference.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The invention is in the field of molecular biology as related to the control of programmed cell death.

2. Description of the Background Art

Programmed Cell Death

Apoptosis, also referred to as programmed cell death or regulated cell death, is a process by which organisms eliminate unwanted cells. Such cell death occurs as a normal aspect of animal development as well as in tissue homeostasis and aging (Glucksmann, A., *Biol. Rev. Cambridge Philos. Soc.* 26:59–86 (1950); Ellis et al., *Dev.* 112:591–603 (1991); Vaux et al., *Cell* 76:777–779 (1994)). Programmed cell death can also act to regulate cell number, to facilitate morphogenesis, to remove harmful or otherwise abnormal cells and to eliminate cells that have already performed their function. Additionally, programmed cell death is believed to occur in response to various physiological stresses such as hypoxia or ischemia. The morphological characteristics of apoptosis include plasma membrane blebbing, condensation of nucleoplasm and cytoplasm and degradation of chromosomal DNA at inter-nucleosomal intervals. (Wyllie, A. H., in *Cell Death in Biology and Pathology*, Bowen and Lockshin, eds., Chapman and Hall (1981), pp. 9–34).

Apoptosis is achieved through an endogenous mechanism of cellular suicide (Wyllie, A. H., in *Cell Death in Biology and Pathology*, Bowen and Lockshin, eds., Chapman and Hall (1981), pp. 9–34) and occurs when a cell activates its internally encoded suicide program as a result of either internal or external signals. The suicide program is executed through the activation of a carefully regulated genetic program (Wylie, A. H., et al., *Int. Rev. Cyt.* 68: 251 (1980); Ellis, R. E., etal.,*Ann. Rev. Cell Bio.* 7:663 (1991)). In many cases, gene expression appears to be required, since cell death can be prevented by inhibitors of RNA or protein synthesis (Cohen et al, *J. Immunol.* 32:38–42 (1984); Stanisic et al., *Invest. Urol.* 16:19–22 (1978); Martin et al., *J. Cell Biol.* 106:829–844 (1988). A genetic pathway of programmed cell death was first identified in the nematode *C. elegans*. In this worm, the products of ced-3 and ced-4 genes carry out the program of cellular suicide (Yuan & Horvitz, *Dev. Bio.* 138: 33 (1990)).

Interleukin-1β Converting Enzyme

The mammalian homologue of the ced-3 gene product is interleukin-1β converting enzyme (ICE), a cysteine protease responsible for the activation of interleukin-1β (IL-1β) (Thomberry, N. A., etal., *Nature* 356: 768 (1992); Yuan, J., et al., *Cell* 75: 641 (1993); Miura, M., et al., *Cell* 75: 653 (1993)). The Ice gene is a member of a family of genes. The mammalian ICE/Ced-3 family now includes at least six members: ICE, ICH-1/NEDD2, CPP32/Yama/Apopain, TX/ICEreIII/ICH-2, ICEreIIII and MCH2 (Yuan et al., *Cell* 75:641–652 (1993); Wang et al., *Cell* 78:739–750 (1994); Kumar et al., *Genes Dev.* 8:1613–1626 (1994); Fernandes-Alnerrni et al., *J. Biol. Chem.* 269:30761–30764 (1994); Tewari, M., et al., *Cell* 81:801–809 (1995); Nicholson, D., et al., *Nature* 376:37–43 (1995); Faucheu, C., et al., *J. Biol. Chem.* 269:30761–30764 (1994); Munday, N. A., et al., *J. Biol. Chem.* 270:15870–15876 (1995); Kamens, J., et al., *J. Biol. Chem.* 270:15250–15256 (1995); Femandes-Alnermi, et al., *Canc. Res* 55:2737–2742 (1994)).

Interleukin-1β converting enzyme (ICE) is a substrate-specific cysteine protease that cleaves the inactive 31 KD prointerleukin-1β at $Asp^{116}$-$Ala^{117}$, releasing a carboxy-terminal 153 amino-acid peptide to produce the mature 17.5 kD interleukin-1β (IL1β) (Kostura et al., *Proc. Natl. Acad. Sci., USA* 86:5227–5231 (1989); Black et al., *FEBS Lett.* 247:386–390 (1989); Cerretti et al., *Science* 256:97–100 (1992); Thomberry et al., *Nature* 356:768–774 (1992)). Since this is member of a family of proteases whose active site cysteine residue is essential for ICE-mediated apoptosis, their proteolytic activity appears critical in mediating cell death (Miura et al.,*J. Cell* 75:653–660 (1993)). IL1β is also a cytokine involved in mediating a wide range of biological responses including inflammation, septic shock, wound healing, hematopoiesis and growth of certain leukemias (Dinarello, C. A., *Blood* 77:1627–1652 (1991); diGiovine et al., *Today* 11:13 (1990)).

A specific inhibitor of ICE, the crmA gene product of cowpox virus, prevents the proteolytic activation of IL-1β (Ray et al., *Cell* 69:597–604 (1992)) and also inhibits host inflammatory response (Ray et al., Cell 69:597–604 (1992)). Cowpox virus carrying a deleted crmA, gene is unable to suppress the inflammatory response of chick embryos, resulting in a reduction in the number of virus-infected cells and less damage to the host (Palumbo et al., *Virology* 171:262–273 (1989)). This observation indicates the importance of ICE in bringing about the inflammatory response.

It has also been shown that ICE overexpression induces apoptosis, and that mature IL-1β is released during cell death (Miura, M., et al., *Cell* 75: 653 (1993); Miura, M., et al., *Proc. Natl. Acad. Sci. USA.* 92:8318–8322, (1995). The cowpox virus gene product CrmA, a member of the serpin family and an inhibitor of ICE also prevents apoptosis (Miura, M., et al., *Cell* 75: 653 (1993); Miura, M., et al., *Proc. Natl. Acad. Sci. USA.* (In press); Ray, C. A., et al., *Cell* 69: 597 (1992); Gagliardini, V., et al., *Science* 263: 826 (1993); Boudreau, N., et al.,*Science* 267: 891 (1995); Enari, M., et al.,*Nature* 375: 78 (1995); Los, M., et al.,*Nature* 375: 81 (1995)). In addition, the ability of CrmA to inhibit apoptosis correlates with its ability to inhibit mature IL-1β production. Recent reports indicate that tumor necrosis factor-α TNF-α) induced apoptosis is mediated through a CrmA-inhibitable pathway suggesting involvement of the ICE family (Tewary, M., et al., *J. Biol. Chem* 270: 3255 (1995); Hsu, H., et al., *Cell* 81: 495 (1995); Miura, M., et al., *Natl. Acad Sci. U.S.A.* (In press)).

While the critical role of the ICE family in cell death is well accepted, the function of mature IL-1β in apoptosis is controversial. IL-1β has been shown to induce apoptosis in some systems (Onozaki et al., *Immun* 135:3962–3968 (1985); Ankarcrona etal., *Exp. Cell Res.* 213:172–177 (1994); Fratelli, M., etal., *Blood* 85:3532–3637 (1995)), and to prevent it in others (Belizario & Dinarello, *Cancer Res.* 51:2379–2385 (1991); Strijbos & Rothwell, *J. Neurosci.* 15:3468–3474 (1995)). Mature IL-1β has not only been detected in the media of TNF-α treated apoptotic fibroblasts, but also in the media of macrophages undergoing apoptosis following *Shigella flexneri* infection (Zychlinsky, A., et al., J. Clin. Invest. 94: 1328 (1994)). The detection of mature IL-1β release during apoptosis provides strong evidence for ICE itself being activated in cell death, since in-vivo ICE is the major (if not the only) protease responsible for the processing of proIL-1β as demonstrated in ICE deficient mice (Li, P., et al., *Cell* 80: 401 (1995); (Kuida, K., et al., *Science* 267: 2000 (1995)).

Tumor Necrosis Factor

Tumor necrosis factor-α (TNF-α) is a pleiotropic tumoricidal cytokine (Tracey, K. J. et al., *Ann. Rev. Cell. Biol.* 9:317–343 (1993)). One of the striking functions of TNF-α is to induce apoptosis of transformed cells. In the case of non-transformed cells, TNFα can also induce apoptosis in the presence of metabolic inhibitors (Tracey, K. J., et al., *Ann. Rev. Cell. Biol.* 9:317–343 (1993). Apoptosis induced by TNF-α is also suppressed by bcl-2.

One of the most extensively studied functions of TNF-α is its cytotoxicity on a wide variety of tumor cell lines in vitro (Laster, S. M. et al., *J. Immunol.* 141:2629–2634 (1988)). However, the mechanism of cell death induced by TNF has been largely unknown. HeLa cells express predominantly p55 TNF receptor which is thought to be responsible for cell death signaling (Englemann, H. et al., *J. Biol. Chem.* 265:14497–14504 (1990); Thoma, B. et al., *J. Exp. Med.* 172:1019–1023 (1990)). Additionally, HeLa cells are readily killed by TNF-α in the presence of the metabolic inhibitor cycloheximide (CHX). The cell death induced by TNF-α/CHX shows DNA fragmentation and cytolysis, which are typical features of apoptosis (White, E. et al., *Mol. Cell. Biol.* 12:2570–2580 (1992)). Expression of adenovirus E1B 19K protein, which is functionally similar to bcl-2, inhibits apoptosis induced by TNF in HeLa cells (White, E. et al., *Mol. Cell. Biol.* 12:2570–2580 (1992)).

SUMMARY OF THE INVENTION

It has now been found that the IL-1β receptor antagonist (IL-1Ra) inhibits apoptosis induced by trophic factor deprivation and by hypoxia. In addition, mature IL-1β itself induces cell death through a pathway independent of CrmA-sensitive gene activity and cooperates with ICE and ICH-$1_L$ in apoptosis. As such, the invention identifies proIL-1β as the first substrate of any apoptosis inducing gene, whose cleavage product is a downstream mediator of the apoptotic cascade.

The invention is first directed to a method of preventing programmed cell death comprising the step of blocking mIL-β receptor binding. Preferably the mIL-β receptor binding is blocked with IL-1RA.

The invention is further directed to a method for inhibiting oncogenic transformation comprising stimulating apoptosis in infected cells. Preferably, the apoptosis is stimulated with IL-1β and/or TNF-α.

The invention is further directed to a method of modulating apoptosis comprising activating the ICE pathway and mIL-1β production.

The invention is further directed to a method of modulating apoptosis comprising priming a cell prior to binding of IL-1 to its receptor. Priming the cell can include inter alia, use of trophic factor deprivation, hypoxia, G1/S phase arrest. This may be followed by IL-1β treatment.

The invention is further directed to a method of inhibiting hypoxia-inducted cell death using an IL-1 receptor blocker. Preferably the IL-1 receptor blocker is selected from the group consisting of IL-1Ra, an anti-IL-1polyclonal neutralizing antibody and an anti-IL-1 type-1 receptor neutralizing monoclonal antibody.

The invention is further directed to a method of preventing cell death resulting from ICH-$1_L$ comprising use of IL-1Ra.

Methods of use are provided. These include, inter alia, methods to either increase or decrease cell death in treating various pathologies, including tumors of specific bodily organs of an animal, including humans. Additionally, one may use the invention to inhibit oncogenic cell transformation, to address complications concerning apoptosis which accompany hypoxia or ischemia in various organs or to screen for agents which affect apoptosis.

BRIEF DESCRIPTION OF THE FIGURES

FIG. 1A: HeLa, and HeLa/CrmA cells incubated for 16 hours under hypoxic conditions with IL-1Ra, IL-1 antibody, and IL-1 type-1 receptor antibody. Results are expressed as the average of 4 independent experiments. Error bars indicate s.e.m. FIG. 1B: IL-1Ra blocks $^{125}$I IL-1β receptor binding in HeLa cells.

FIG. 2: IL-1Ra extends neuronal survival following trophic factor deprivation. Results are expressed as the average of 3 independent experiments. Error bars indicate S.E.M.

FIG. 3A: Percent cell death in L929 cells treated with TNF-α alone (▲) and TNF-α plus IL-1Ra (●). FIG. 3B: Percent cell death in HU arrested, TNF-α (Symbols are the same as in FIG. 3A). FIG. 3C: Percent cell death in IL- treated HeLa cells (▲), HeLa /Crm (■), and HeLa cells treated with IL-1Ra (●). Results are expressed as the average of 3 independent experiments. Error bars indicate S.E.M. Phase contrast and fluorescent photomicrographs of: FIG. 3D: HU arrested cells, FIG. 3E: treated with TNF-α or FIG. 3F: IL-1β; and stained with Hoechst dye (FIGS.: 3G–3I) showing condensed and fragmented nuclei.

(FIGS. 5A–5B), Ice (FIGS. 5C–5D), or proIL-1β and Ice (FIGS. 5E–5G). COS cells transfected with proIL-1β and immunostained anti-human polyclonal IL-1 antibody and a secondary RITC coupled antibody is alive as demonstrated by their nuclear morphology and morphologic appearance. Cells transfected with Ice and immunostained with a anti-human ICE monoclonal antibody and a secondary FITC conjugated antibody appears morphologically normal, however its nucleus is condensed suggesting initiation of apoptotic pathways, but in the absence of IL-1β it can not be completed. Coexpression of both Ice and proIL-1β induces typical apoptotic features (condensed nucleus and round morphology).

FIG. 6A: Preincubation with exogenous mature IL-1β (HeLa/IL-β), inhibits hypoxia-mediated apoptosis in HeLa cells. FIG. 6B) $^{125}$I IL-1β down-regulates the IL-1β receptor in HeLa cells.

FIG. 7: The cDNA sequence (SEQ ID. No:1) of Ich-$1_L$ and the deduced amino acid sequence (SEQ ID. NO:2) of the Ich-$1_L$ protein product.

DETAILED DESCRIPTION

Figure 1A:
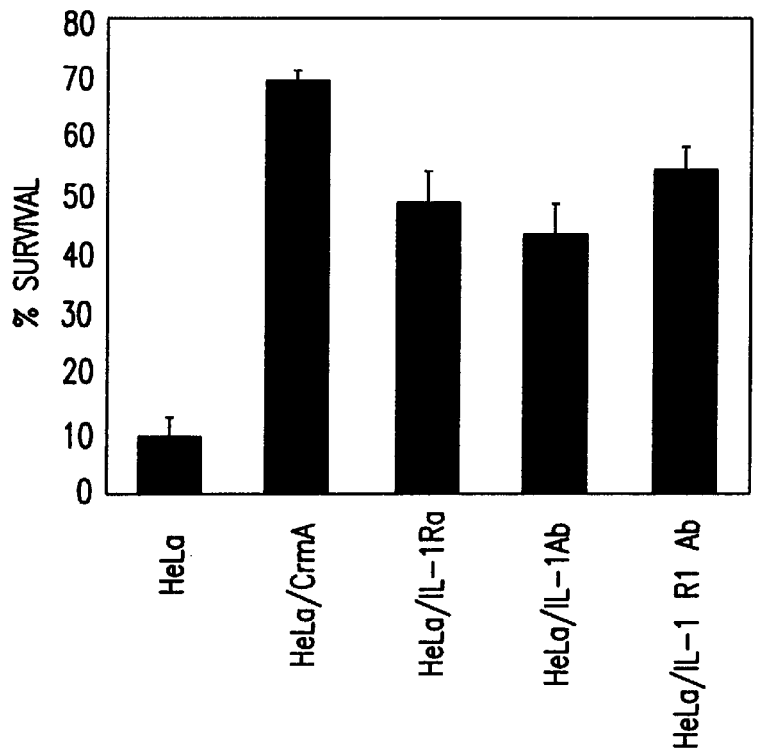
FIGS. 1A–1B: Hypoxia-induced apoptosis is inhibited by CrmA, IL-1Ra, anti-IL-1 Ab, anti-IL-1 type-1 receptor antibody, and mature IL-1β.

In the description that follows, a number of terms are used extensively. In order to provide a clearer and more consistent understanding of the specification the following definitions are provided.

Definitions

Italicized words such as Ice, ICE or Ich refers to the gene, while "ICE, Ich or ICH" refers to the gene product encoded by the corresponding gene.

Apoptosis should be understood to refer to the process by which organisms eliminate unwanted cells. The process is carefully regulated by a cellular program. Apoptosis may eliminate cells during normal development, aging, tissue homeostasis or following imposition of an external stress such as hypoxia or trophic factor deprivation.

Hypoxia should be understood to refer to a condition where the oxygen concentration available to a cell is decreased relative to normal levels. The most extreme hypoxia would be almost a total lack of oxygen (referred to as anoxia).

ICE pathway should be understood to refer to that pathway by which interleukin converting enzyme converts the pro-IL$\beta$ to IL-$\beta$ eventually resulting in programmed cell death.

Blocking IL-1-mediated signal transduction should be understood to refer to using any compound or chemical which blocks the action of IL-1 at the IL-1 receptor. The signal transduction may be blocked by an immunoglobulin (such as, a monoclonal or polyclonal antibody or active fragments of such antibody) including for example an anti-IL-1polyclonal neutralizing antibody or an anti-IL type-1 receptor neutralizing monoclonal antibody. Alternatively, the signal transduction may be blocked by non-immunoglobulin compounds (such as polypeptides, organic compounds, etc.) including for example IL-1 Ra which is a naturally occurring cytokine that binds to the IL-1 receptor. Alternatively, signal transduction may be blocked by any competitive or non-competitive inhibitor of IL-1$\beta$.

Trophic factor deprivation should be understood as the removal of factors (e.g. serum or NGF) which are required for cell survival. Absence of such factors activates the apoptotic pathway.

$G_1$/S phase arrest should be understood to be an event which occurs to a cell that causes it to fail to transit from the $G_1$ to the S phase of the cell cycle. The transition from $G_1$ to S is considered the most critical step of the cell cycle (Chiarugi et al. *Cell. Mol. Biol. Res.* 40:603–612, 1994).

Modulating apoptosis should be understood to be any action which alters the level of cell death in either a positive or a negative direction. Ways in which to measure such changes are readily known to those of skill in the art, but may include inter alia, trypan blue exclusion, chromium release, specific changes in cell morphology including plasma membrane blebbing, condensation of nucleoplasm and cytoplasm and degradation of chromosomal DNA at inter-nuceosomal intervals. Additional methods include metabolic assays such as the MTT (3-[4,5-D, methyl-thiazole-yi]-2,5-diphenyltetrazolium bromide; thiazolyl blue) assay or viability measurement by FACS analysis.

Priming a cell should be understood to be an event or treatment which the cell undergoes such as trophic factor deprivation, hypoxia or $G_1$/S phase arrest that is required in order for IL-1$\beta$ to activate the cell death program. In vivo this may also include any process which makes a cell "ill," e.g. a pathological condition, and thereby ready-to be eliminated from the organism.

Ich-$1_L$ and Ice should be understood to be cell death genes. Ich-$1_L$ has the sequence (SEQ. ID.NO. 1 and SEQ. ID.NO. 2) shown in FIG. 7. Ich-$1_L$ is a fragment of the Ich-1 gene. The Ich-1 gene is homologous to other cell death genes including, inter alia, nedd2. Ich-1 contains the QACRG sequence characteristic of cell death genes. The sequence of human ICE can be found in Thomsberr et al., *Nature* 356:768–774, 1992.

Naturally occurring cell death acts to regulate cell number, to facilitate morphogenesis, to remove harmful or otherwise abnormal cells and to eliminate cells that have already performed their function. Additionally, programmed cell death is believed to occur in response to physiological stresses such as hypoxia or ischemia.

Acute and chronic disregulation of cell death is believed to lead to a number of major human diseases (Barr et al. *Biotech.* 12:487–493, 1995). These diseases include but are not limited to malignant and pre-malignant conditions, neurological disorder, heart disease, immune system disorders, intestinal disorders, kidney disease and aging.

Malignant and pre-malignant conditions may include solid tumors, B cell lymphomas, chronic lymphocytic leukemia, prostate hypertrophy, preneoplastic liver foci and resistance to chemotherapy. Neurological disorders may include stroke, Alzheimer's disease, prion-associated disorder and ataxia telangiectasia. Heart disease may include ischemic cardiac damage and chemotherapy-induced myocardial suppression. Immune system disorder may include AIDS, type I diabetes, lupus erythematosus, Sjogren's syndrome and glomerulonephritis. Intestinal disorder may include dysentery, inflammatory bowel disease and radiation- and HIV-induced diarrhea. Kidney disease may include polycystic kidney disease and anemia/erythropoiesis. Specific references to these pathophysiological conditions as involving disregulated apoptosis can be found in Barr et al. Id.- Table I.

Knowing the genes and substrates involved in the ICE pathway leads to means for intervention of cell death thereby altering apoptosis. Such knowledge can also lead to development of assays for agents which may affect the apoptotic process. Interventions may include, inter alia, agents which affect the activities of the gene products (e.g. agents which block receptors), modulation of the gene product using gene-directed approaches such as anti-sense oligodeoxynucleotide strategies, transcriptional regulation and gene therapy (Karp et al., *Cancer Res.* 54:653–665 (1994)). Therefore, apoptosis should be amenable to therapeutic intervention. In this regard, one may either stimulate or inhibit the process depending upon whether wants to increase or decrease the rate of programmed cell death.

Proteolytic cleavage by the ICE family may lead to apoptosis in several ways. One possibility is that cleavage of a large number of proteins destroys the entire cellular machinery. This, however, is unlikely because most proteins appear to remain intact when cells undergo apoptosis (Lazebnik et al., *Nature* 371:346–347 (1994)). The second possibility is that proteolytic cleavage of one critically important substrate leads to cell death. This also is unlikely because a number of proteins, including pro-IL-1$\beta$ ribose polymerase (PARP), U1-70 kD ribonuclear protein, and nuclear lamin are cleaved during apoptosis (Miura, et al., *Proc. Natl. Acad. Sci.* 92:8318–8322 (1995); Lazebnik et al., *Nature* 371:346–347 (1994); Casciola-Rosen et al., *J. Biol. Chem* 269:30757–30760 (1994); Lazebnik, Y. A., et al., *Proc. Natl. Acad. Sci.* 92:9042–9046 (1995)). It is not clear (with the exception of pro-IL-1$\beta$), whether the cleavage products of these proteins mediate downstream events of cell death pathways or whether they are merely the end result of apoptosis. The third possibility is that activation of the ICE pathway and therefore the ICE family may result in cleavage of several substrates, some being activated (mediating cell death) and others being destroyed (required for cell survival). Activation of the pathway may occur due to events such as trophic factor deprivation, hypoxia, $G_1/S$ arrest or TNF-α treatment. The results obtained in the examples of the specification, leads to favoring the last hypothesis because the data indicate that endogenously-produced mature IL-1β is directly involved in cell death and is the first identified substrate of an apoptosis-inducing gene whose product plays a direct role in mediating the apoptotic cascade. This proposed mechanism, however, should in no way whatsoever be construed as limiting the claims of the invention to operation by such a mechanism.

Additionally, a number of signal transduction mechanisms mediate the biological effect of IL-1β. Several of these second messengers have been implicated in apoptosis and, following ICE activation, likely mediate cell death following endogenous mature IL-1β receptor binding. Therefore, blocking receptor binding will modulate apoptosis. IL-1β induces ceramide production in EL4 thymoma cells (Mathias, S., et al., *Science* 259:519–522 (1993)). IL-1β also induces apoptosis in pancreatic Rlm5F cells via a pathway which is dependent on its ability to induce nitric oxide production (Ankarcrona et al., *Cell Res.* 213:172–177 (1994)). Both ceramide and nitric oxide are strong candidates for direct mediators of apoptosis (Ankarcrona et al., *Cell Res.* 213:172–177 (1994); Haimovitz-Friedman, A., et al., *J. Exp. Med.* 180:525–535 (1994)). A recent report showed that NGF deprivation of PC12 cells, which induces apoptosis, led to a substantial activation of the JNK and p38 MAP kinases (Xia et al., *Science* 270:1326–1331 (1995)). IL-1β has been shown to activate the JNK-p38 signaling pathway and NGF withdrawal may induce secretion of IL-1β which then activates the JNK-p38 pathway and cell death (Raingeaud, J., et al., *J. Biol. Chem.* 270:7420–7426 (1995)).

Having now generally described the invention, the same will be more readily understood through reference to the following examples which are provided by way of illustration, and are not intended to be limiting of the present invention, unless specified.

EXAMPLES

The role played by secreted mature IL-1β in apoptosis induced by trophic factor deprivation of primary dorsal root ganglia (DRG) neurons, and by hypoxia or by TNF-α in L929 and HeLa cells was investigated. The requirement for proIL-1β in apoptosis induced by ICE and ICH-$1_L$ was also evaluated. The results indicated that endogenously produced mature IL-1β plays an integral role in these apoptotic models, and since ICE is the major (if not the only) enzyme to process proIL-1β this provides further evidence for a role of ICE in apoptosis.

Example 1

Effects of Hypoxia

BCL-2 (B-cell lymphoma-2 gene encoded protein) and p53 have been implicated in hypoxia-mediated apoptosis (Shimizu, S., et al., *Nature* 374:811–813 (1995); Jacobson & Raff, *Nature* 374:814–816 (1995); Graeber, T. G., et al., *Nature* 379:88–91 (1996)). To investigate if the ICE family is involved in hypoxia-induced apoptosis, it was tested whether CrmA could inhibit this process.

Hypoxia-induced apoptosis was studied as follows. HeLa and HeLa/CrmA cells (Miura, M., et al., *Proc. Natl. Acad. Sci. USA.* 92:8318–8322, 1995) were seeded in 35 mm dishes at a density of $6\times10^4$/dish in DMEM/10% FCS and grown overnight. The medium was then changed and factors were added (IL-1Ra, R & D, Minneapolis, Minn.), IL-1 antibody (Calbiochem, San Diego, Calif.), or IL-1 type-1 receptor antibody (R & D, Minneapolis, Minn.). Dishes were placed in an anaerobic chamber with a BBL GasPack Plus (Becton-Dickenson, USA), which reduced the oxygen concentration to less than 100 p.p.m. within 90 minutes. After 16 hours, cells were removed from the chamber, immediately trypsinized and scored for viability by trypan blue exclusion. Inhibition of $^{125}$I IL-1β binding by IL-1Ra which was added for 2 hrs at 37° C. After addition of BSA (1 mg/ml) to the medium, cells were incubated at 4° C. for 15 minutes, and then $^{125}$IL-1β (100 ng/ml) was added at 4° C. for 1 hr. For detection of $^{125}$IL-1β binding, cells were treated with 50 mM glycine-HCl, pH 2.6 for 1 min, and quantitated by γ-counting.

Figure 1B:
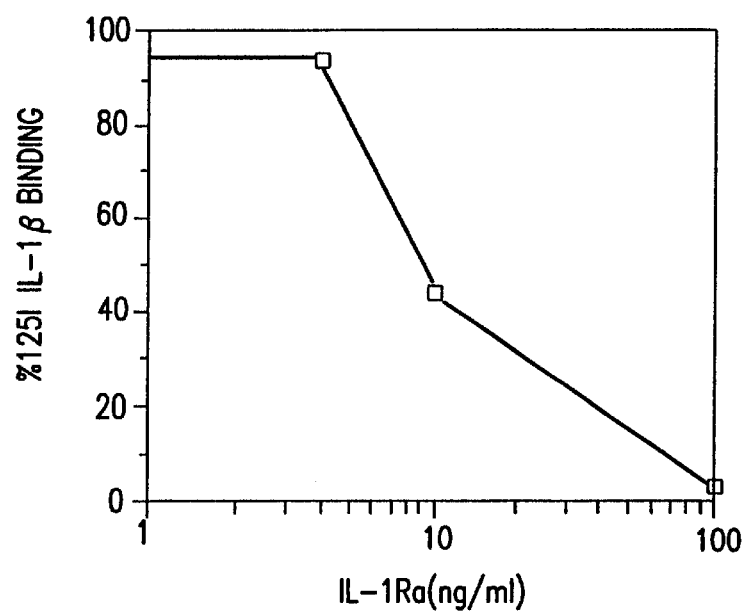

Survival of HeLa cells cultured for 16 hours under hypoxic conditions was 10.1%, compared with 69.0% survival of HeLa cells which stably express CrmA (HeLa/CrmA) (FIG. 1a). Thus, CrmA-inhibitable members of the ICE family play an important role in hypoxia-induced apoptosis. To address whether endogenously produced mature IL-1β plays a role in hypoxia-induced cell death, several methods were employed to prevent IL-1 from binding to its receptor. IL-1Ra (a naturally occurring cytokine which binds to the IL-1 receptor, blocking IL-1 mediated signal transduction) (Dripps, et al., *J. Biol. Chem.* 266:10331–10336 (1991); Granowitz, et al., *J. Biol. Chem.* 266:14147–14150 (1991)), an anti-IL-1 polyclonal neutralizing antibody, and an anti-IL-1 receptor neutralizing monoclonal antibody (the type-1 receptor mediates IL-1 signal transduction) were used. Each of these reagents inhibited hypoxia-induced cell death, suggesting that hypoxia activates an ICE-like, CrmiA-inhibitable pathway, and that endogenously produced mature IL-1β, plays a role in hypoxia-induced cell death by binding to the IL-1 type-1 receptor (FIG. 1a). It was also evaluated and confirmed that IL-1Ra indeed blocks $^{125}$I-IL-1β binding (FIG. 1b) (Dripps, et al., *J. Biol. Chem.* 266:10331–10336 (1991); Granowitz, et al., *J. Biol. Chem.* 266:14147–14150 (1991)).

Example 2

Apoptosis amd Trophic Factor Deprivation in Dorsal Root Ganglia

The role in apoptosis of endogenous IL-β was next investigated. Primary dorsal root ganglia (DRG) neurons undergo apoptosis in culture upon NGF withdrawal (Davies, A. M., ]Development 100: 1019 (1987)). It was previously shown that chicken DRG neuronal death induced by trophic factor deprivation is inhibited by CrmA, suggesting involvement of the ICE family (Gagliardi, V. et al., *Science* 283:826–828 (1993)). To test if endogenously produced mature IL-1β, which is produced by neurons in culture (Freidin et al., *Proc. Natl. Acad. Sci. U.S.A.* 89:10440–10443 (1994) plays a role in trophic factor withdrawal-mediated DRG neuronal apoptosis the human IL-1 receptor antagonist (IL-1Ra) was used. IL-1Ra binds to type I and II IL-1 receptors, blocking the IL-1 signal (Dripps, D. J, etal., *J. Biol. Chem.* 266: 10331 (1991); Granowitz, E. V., etal., *J. Biol. Chem.* 266: 14147 (1991)).

Neuronal trophic factor deprivation was assayed as follows. Post-natal day 1 mouse DRG neurons were isolated, dissociated with trypsin for one hour at 37° C., and plated in a 8 camber poly-lysine/laminin (Sigma, St. Louis, Mo.)

coated slide. Wells were seeded at approximately 1000 neurons/well (8 wells/mouse). Neurons were cultured in Ham's nutrient F-12 supplemented with 20% FCS (Biowhittaker, Walkesvill, Md.), NGF (200 ng/ml) (Sigma, St. Louis, Mo.), BDNF (100 ng/ml) (Preprotech, Rocky Hill, N.J.), glutamine (2 mM), and penicillin/streptomycin. The medium was replaced daily with either trophic factor containing medium (TF(+))=20% FCS and NGF (200 ng/ml), or trophic factor deficient medium, TF(−)=serum and NGF-free medium in the presence of saturating concentration of mouse NGF monoclonal antibody (100 ng/ml) (Boehringer Mannheim, Indianapolis, Ind.), and IL-IRA (100 ng/ml unless otherwise indicated in the text). Healthy neurons were counted under a phase contrast microscope 24 and 48 hours following the media change.

IL-1Ra (100 ng/ml) inhibited trophic factor withdrawal-induced apoptosis by 69.2% and 37.8% in 24 and 48 hours respectively (FIG. 2). Inhibition of neuronal apoptosis by IL-1Ra was dose dependent (43.5% in 24 hours at a concentration of 40 ng/ml). These results suggest that endogenously produced mature IL-1β plays a role in neuronal apoptosis following trophic factor withdrawal. However, even though neurons have been shown to produce mature IL-1β in culture, it can not be excluded that in this mixed cell population, mature IL-1β is not of non-neuronal origin (Freidin, M., et al., *Proc. Natl. Acad. Sci. U.S.A.* 89: 10440 (1992)). For this reason, several cell line systems were tested to determine if IL-1Ra had similar anti-apoptotic properties.

Example 3

TNF-α and Apoptosis

TNF-α induces apoptosis via a CrmA-inhibitable pathway (Gagliardini, V., et al., *Science* 263: 826 (1993); Boudreau, N., et al., *Science* 267: 891 (1995); Enari, M., et al., *Nature* 375: 78 (1995); Los, M., et al, *Nature* 375: 81 (1995); Tewary, M., etal., *J. Biol. Chem.* 270: 3255 (1995); Hsu, H., et al., *Cell* 81: 495 (1995)). In addition it has been demonstrated that mature IL-1β is secreted by TNF-α treated cells undergoing apoptosis, suggesting ICE activation during this process (Miura, M., et al., *Proc. Natl. Acad. Sci U.S.A.* 92:8318–8322, 1995).

The role of secreted mature IL-1β plays a role in TNF-α induced apoptosis of L929 and HeLa cells was examined.

HeLa, HeLa/CrmA, and L929 cells were seeded ($2\times10^4$) in a 24 well plate and grown overnight in DMEM with 10% FCS. After 12 hours, the cells were washed 3 times with serum free DMEM, and hydroxyurea (HU) (2.5 mM) (Sigma, St. Louis, Mo.) was added to the HeLa and HeLa/CrmA cells Meikrantz, W., et al., *Proc. Natl. Acad. Sci. U.S.A.* 91: 3754 (1994)). After five hours, IL-1Ra (40 ng/ml) was added to the appropriate wells, and one hour later either TNF-α or mature IL1β were added. Twenty-four hours later, IL-1Ra was again added to the appropriate wells, and cell death was evaluated by trypan blue exclusion 60 hours after the initial addition of HU. Each condition was done three times in duplicate and 200 cells counted per well. For the photographs cells were grown on 2 well slides, and for nuclear morphology determination cells were fixed in 4% paraformaldehyde and incubated with Hoechst dye #33258 (10 µg/ml) (Sigma, St. Louis, Mo.).

Figure 3A:
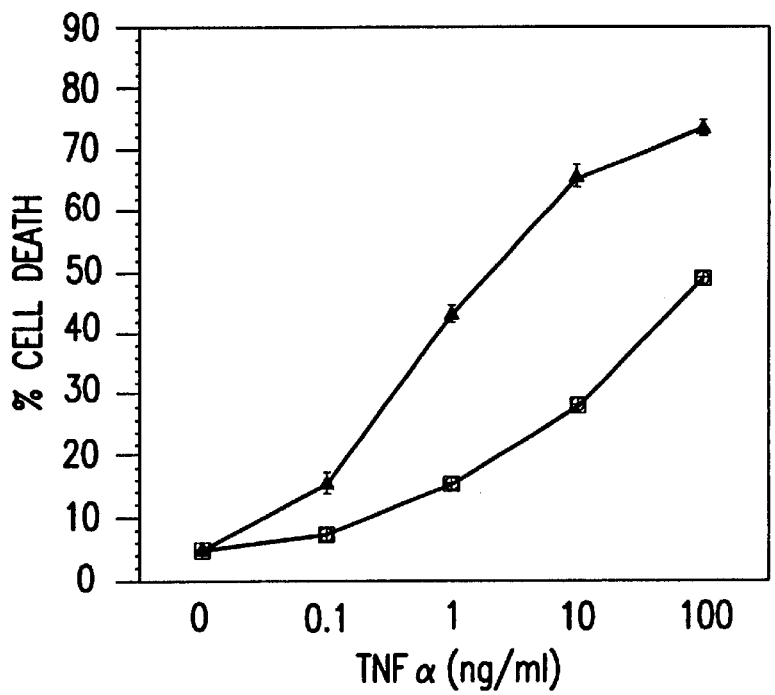
FIGS. 3A–3I: Apoptosis induced by TNF-α and mature IL-1βis mediated by an IL-1Ra inhibitable pathway.

IL-1Ra protected L929 cells from TNF-α induced death by up to 64.9%, suggesting that secretion and receptor binding of mature IL-1β is an integral component of TNF-a induced cell death (FIG. 3*a*).

Figure 3B:
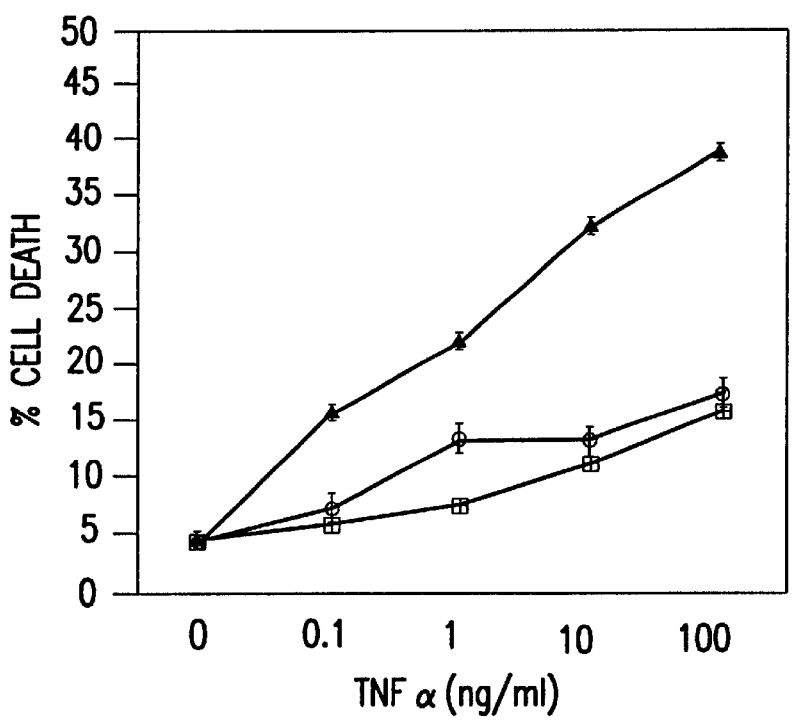

In addition, hydroxyurea (HU) treated, $G_1/S$ phase arrested HeLa cells are induced to undergo programmed cell death by TNF-α (Meikrantz, W., et al., *Proc. Natl. Acad. Sci. U.S.A.* 91: 3754 (1994)). Under this conditions, IL-1Ra also inhibited HeLa cell death by 56.0% (FIG. 3*b*). HeLa cells induced to die by TNF-a and cyclohexamide were also protected by IL-1Ra as well as by three different neutralizing IL-1 antibodies (data not shown). HeLa/CrmA cells were protected from TNF-α induced apoptosis by 59.5%, suggesting that an ICE-like activity is involved in the cell death signaling pathway mediated by this cytokine (FIG. 3*b*).

Example 4

Mature ID/IL-β in Apoptosis

Mature IL-1β alone does not induce apoptosis of most healthy proliferating cells (including HeLa and L929). To examine if IL-1β would induce cell death in $G_1/S$ phase arrested cells, HU treated HeLa cells were exposed to this cytokine.

Figure 3C:
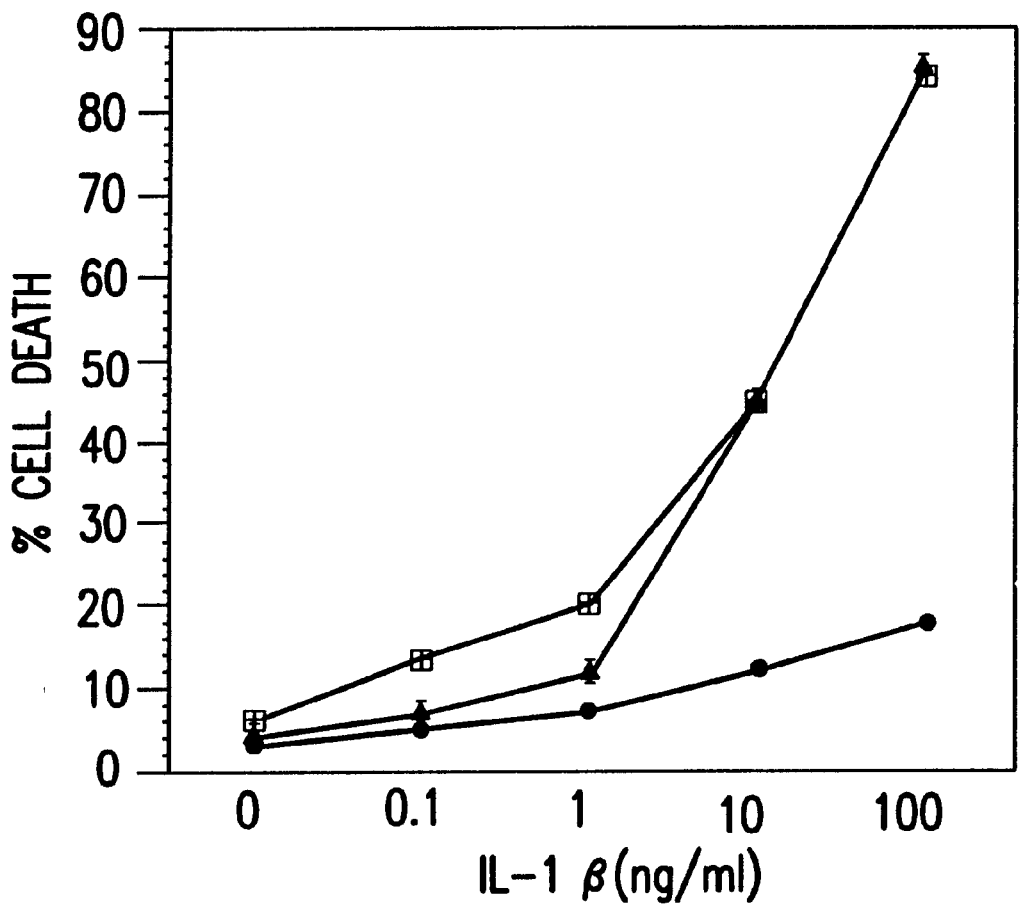
Figure 3D:
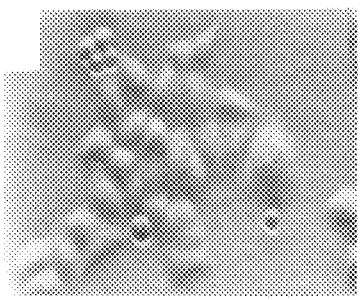
Figure 3E:
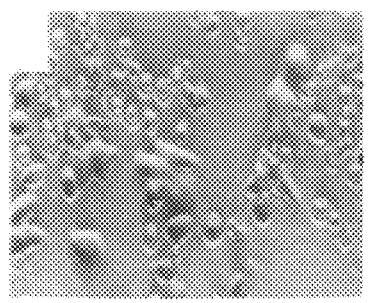
Figure 3F:
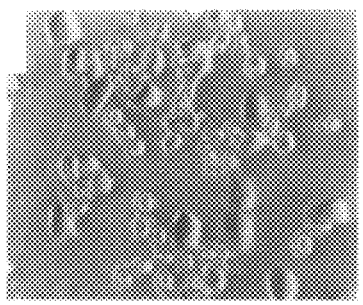
Figure 3G:
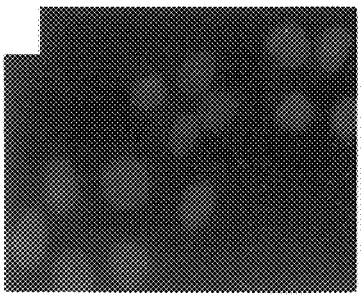
Figure 3H:
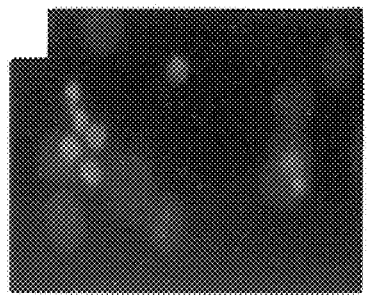
Figure 3I:
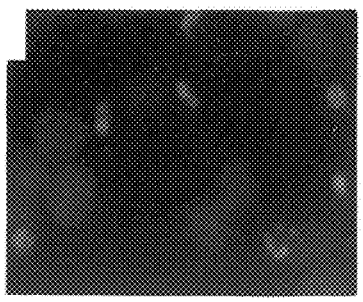
Figure 4A:
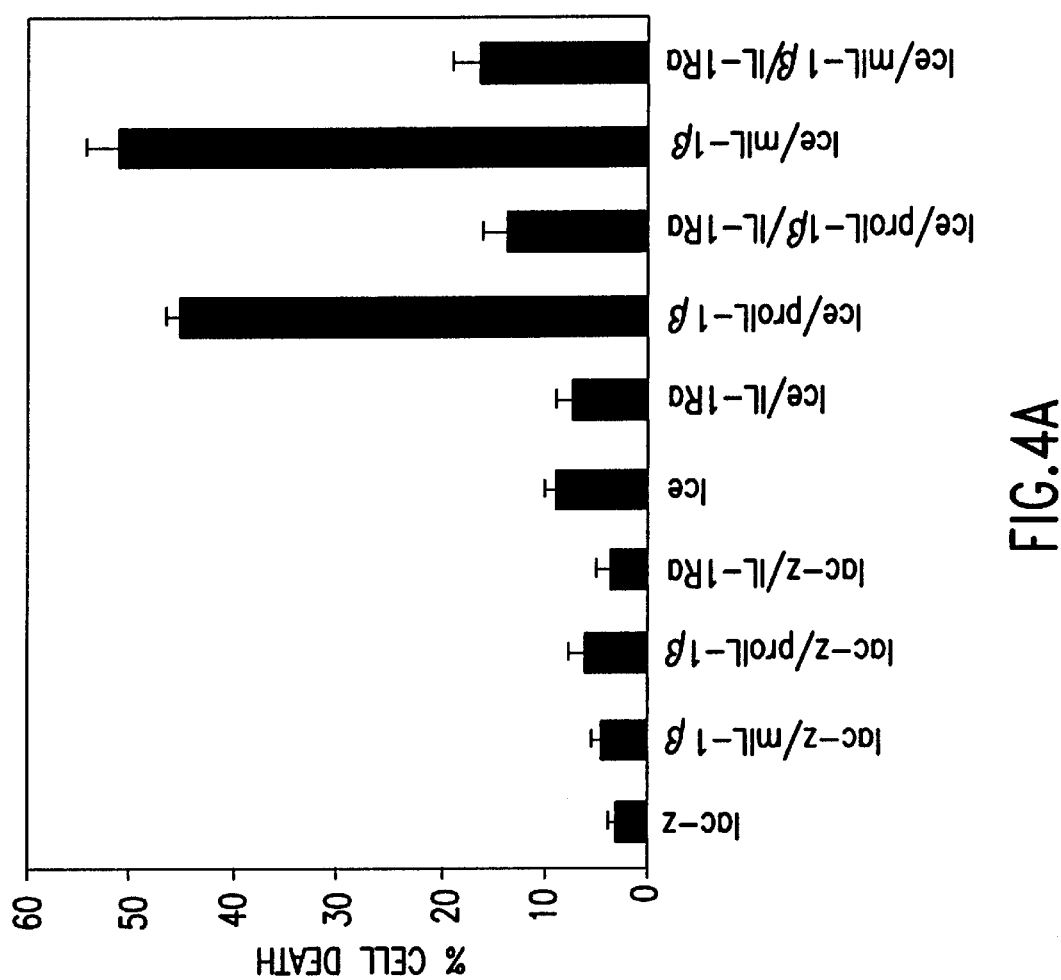
FIGS. 4A–4D: ICE requires mature IL-1β extracellular receptor binding for the induction of apoptosis in COS cells. Percentage of cell death (FIG. 4A), and X-gal staining of COS cells 36 hours following transfection with Ice (FIG. 4B), Ice and pro-IL-1β (FIG. 4C), Ice treated with mature IL-1β(FIG. 4D). Results are expressed as the average of 3 independent experiments. Error bars indicate s.e.m.
Figure 4B:
Figure 4C:
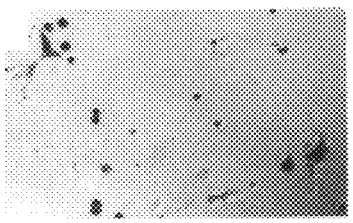
Figure 4D:
Figure 5A:
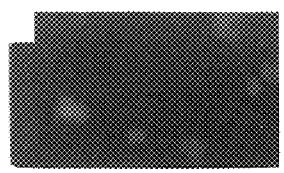
FIGS. 5A–5G: Immunofluorescence of COS cells transiently transfected with proIL-1β.
Figure 5B:
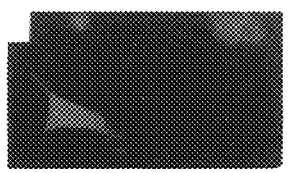
Figure 5C:
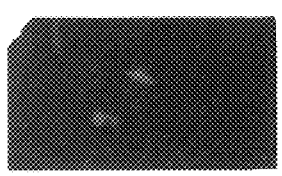
Figure 5D:
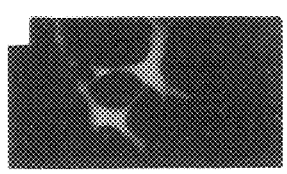
Figure 5E:
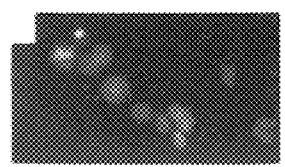
Figure 5F:
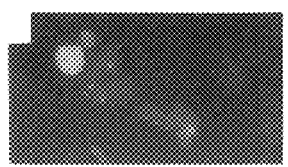
Figure 5G:
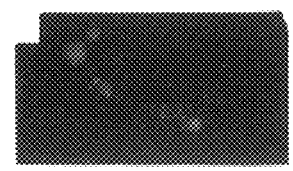

$G_1/S$ phase arrested HeLa cells treated with exogenous mature IL-1β died in a dose dependent fashion (83.7% at 100 ng/ml), which was inhibited by the addition of IL-1Ra (FIG. 3*c*). HU arrested, mature IL-1β and TNF-α treated cells underwent typical apoptotic changes of cellular shrinkage, nuclear condensation, and fragmentation (FIG. 3*d*–FIG. 3*i*). It is interesting that HeLa/CrmA cells are not protected from mature IL-1β as they are from TNF-α killing, suggesting that mature IL-1β induces the apoptotic cascade distal to ICE, and in HU treated cells this cytokine causes cell death through an ICE-independent pathway (FIG. 3*c*). This indicates that CrmA is indeed blocking an ICE-like function and that production and secretion of mature IL-1β is a downstream effector of the apoptotic TNF-α/ ICE cascade. HeLa cells, however, are required to be primed (in this case with HU arrest) to establish the appropriate intracellular milieu to be sensitized to mature IL-1β induced apoptosis. HU treatment likely mimics intracellular signals which are part of the apoptotic cascade.

Example 5

Pro-IL1β Processing and Apoptosis

It was next directly investigated whether proIL-1β processing was required for ICE-mediated apoptosis. For this purpose COS cells were used. These cells are unusual because they are resistant to cell death induced by Ice and Ich-$1_L$ over-expression (Wang, L., et al., *Cell* 78: 739 (1994)).

COS cells were plated ($2\times10^4$) in 6-well plates in DMEM with 10% FCS. After 12 hours the wells were washed with serum and antibiotic free medium, and transfected using lipofectamine with either Ice-lacZ, Ich-$1_L$-lacZ, βactin-lacZ(1 µg) or with proIL-1β (0.5 µg) for 3 hours. The sequence for Ich-$1_L$ is shown in FIG. 7 and the sequences of human ICE and pro- IL-1β are found respectively in Thornsberry et al., *Nature* 356:768–774 (1992) and in *J. Immunol.* 137:3644–3648, 1986. The medium was then removed and DMEM with 10% FCS added. IL-1Ra (40 ng/ml) was then added to the appropriate wells, and after one hour IL-1β (100 ng/ml) was added. X-gal reaction was performed 36 hours following the transfection and percentage of round blue (dead) cells were scored (Miura, M., et al., *Cell* 75: 653 (1993))

Transfection of Ice or Ich-$1_L$ into Rat-1 cells induces 94.2% and 92.1% cell death respectively within 24 hours (Wang, L., et al., *Cell* 78: 739 (1994)). In contrast, COS cells transiently expressing Ice-lacZ, Ich-$1_L$lacZ or pro-IL-1β genes for 36 hours, died 9%, 21%, and 6.3% respectively. However, COS cells coexpressing lce-lacZ and proIL-1β or Ich-1$_L$lacZ and proIL-1β, died 51.0% and 57.3%, respectively. In addition, treatment of Ice-lacZ or Ich-1$_L$-lacZ transfected cells with extracellular mature IL-1β or TNF-α efficiently induced cell death Results of treatment of Ice-lacZ transfected cells with IL-1β are shown in FIG. 4. Exogenous mature IL-1β and TNF-α did not induce apoptosis in COS cells, indicating that ICE and ICH-1$_L$ have substrates in addition to proIL-1β required for cell death and that in COS cells, following ICE activation, IL-1β signal transduction is required for the induction of apoptosis. IL-1Ra significantly inhibited the death of COS cells expressing Ice-lacZ and proIL-1β or Ich-1$_L$-lacZ and proIL-11β, and of Ice-lacZ or Ich-1$_L$-lacZ in the presence extracellular TNF-α or mature IL-1β. This indicates a role for mature IL-1β in the induction of apoptosis following ICE family activation.

Dual immunofluorescence staining (with anti-ICE and anti-IL-1 antibodies) of COS cells cotransfected with Ice and proIL-1β indicates that only cells expressing both ICE and proIL-1β, but not either protein alone undergo apoptosis (FIG. 5). It was consistently noticed that nuclei of cells transfected with Ice are smaller than that of control cells (FIG. 5c). These cells are alive as demonstrated by their flat morphology and adherence to the plate (FIG. 5d), suggesting that ICE initiates the apoptotic process but requires additional factors (i.e. mature IL-1β or TNF-α) for the complete execution of the cell death pathway.

The method for the dual immunofluorescent staining was as follows. COS cells ($1.5 \times 10^4$) were plated in a poly-lysine coated two chamber slide, and after 12 hours transfected as described above. Cells were fixed after 36 hours with 4% paraformaldehyde (15 min,), blocked with I % heat inactivated goat serum/2% BSA in PBS (2 hours) and incubated with a rabbit polyclonal IL-1 (1:300)(Calbiochem) and a hybridoma supernatant mouse monoclonal human ICE antibodies (12 hours at 4° C.), chambers were washed 3x with PBS, and incubated with a goat anti-mouse FITC-labeled, a goat anti-rabbit RITC-labeled antibodies (1:200)(Cappel), and Hoechst dye #33258(10 μg/ml) for 45min. Cells were rinsed 3x with PBS. Slides were examined with an axioplan microscope and photographed with a 40x objective.

Example 6

Inhbition of hypoxia-induced Apoptosis

It was determined whether exogenous mature IL-1β preincubation inhibits cell death in a system where ICE activation, and mature IL-1β receptor binding are important for apoptosis.

Hypoxia was produced as described in Example 1. IL-1β (100 ng/ml) was added as the cells were placed into the hypoxia chamber (90 min. are required to reach oxygen concentrations of 100 p.p.m.). IL-1 receptor binding assay: HeLa cells ($10^6$) were seeded in 10 cm dishes and grown overnight. Media was then exchanged containing 1 mg/ml of BSA and 100 ng/ml of $^{125}$I IL-1β at 4° C. for 1 hr. After washing twice with cold medium, the cells were incubated with fresh warm medium at 37° C. for 0, 30, 60 and 120 minutes. Cells were then treated as above with glycine and radioactivity scored.

Figure 6A:
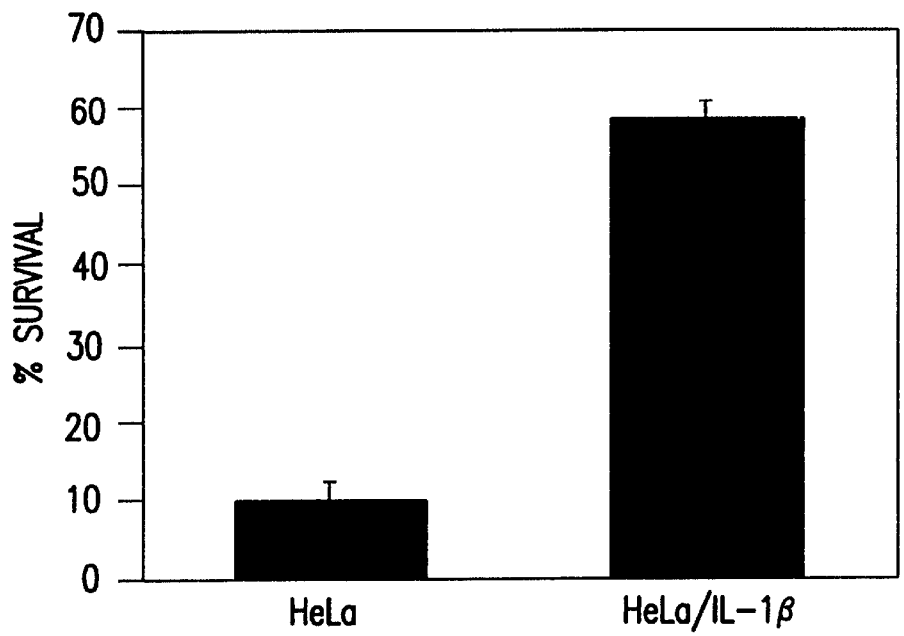
FIGS. 6A–6B.
Figure 6B:
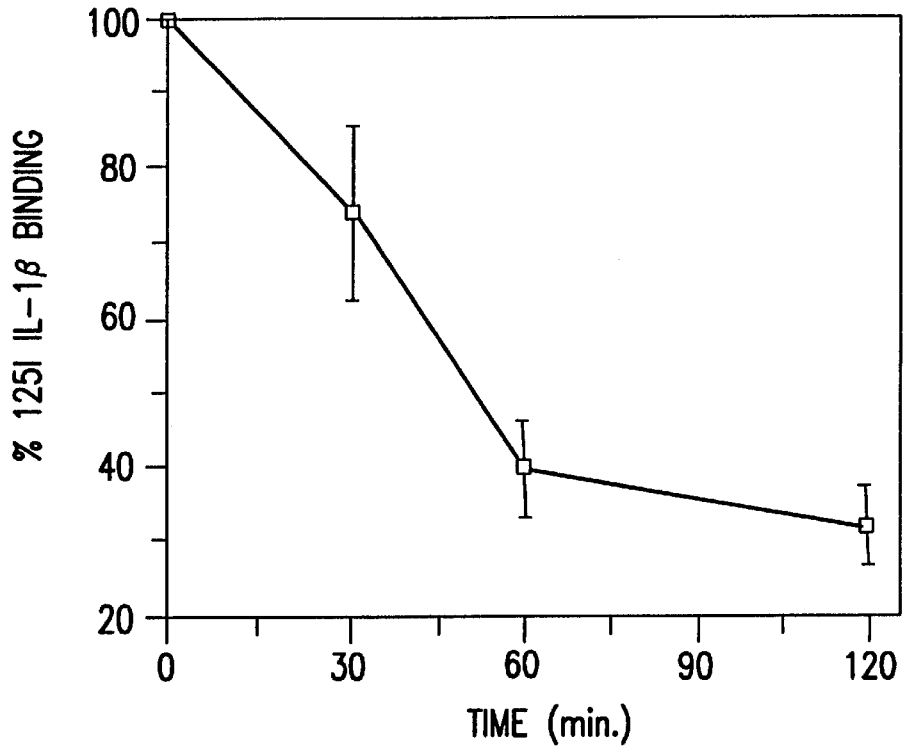

HeLa cells preincubated with exogenous IL-1β were markedly protected from hypoxia-induced cell death (10.1% vs. 58.7% survival) (FIG. 6a). To explain the inhibition of apoptosis by IL-1β, it was investigated whether preincubation with exogenous IL-1β in the system prior to exposure to apoptotic stimuli, down-regulates the IL-1 receptor. Indeed, receptor binding assays demonstrated that exogenous IL-1β significantly down-regulated the IL-1 receptor (FIG. 6b). Down-regulation of the IL-1 receptor, in part explains the protective role of exogenous IL-1β when added prior to the induction of apoptosis. The effect of IL-1β receptor binding on apoptosis is dependent on whether ICE is active (enhancing cell death), or if ICE is inactive (inhibiting cell death, in part by down-regulating the IL-1 receptor).

The results presented in the Examples have identified proIL-1β as the first substrate of an apoptosis inducing gene directly involved in cell death, whose processing, secretion, and extracellular receptor binding play an integral role in the ICE apoptotic cascade. IL-1β is believed to cause cell death by inducing ceramide and/or nitric oxide production, both of which have been shown to be involved in apoptosis (Mathias, S., et al., *Science* 259: 519 (1993); Haimovitz-Friedman, et al., *J. Exp. Med* 180: 525 (1994); Ankarcrona, M., et al., *Exp. Cell Res.* 213: 172 (1994)). The results reconfirm that a variety of apoptotic stimuli (trophic factor deprivation, hypoxia, and TNF-α) activate ICE (or another IL-1β convertase), and that cell death can be inhibited by either blocking ICE activity with CrmA or by blocking IL-1β receptor binding with IL-1Ra.

The fact that IL-1Ra did not fully inhibit apoptosis likely occurs for the following reasons. Since occupancy of only a few IL-1receptors (approximately 5 per cell) are necessary for a complete activation of the IL-1 biological response (Dinarello, C. A., *FASEB J.* 8: 1314 (1994)), IL-1Ra, being a competitive inhibitor, does not likely fully displace all the IL-1β from its receptor, and hence only protecting a portion of cells. Alternatively, following ICE activation, mature IL-1β might act by enhancing cell death pathways, via the induction of ceramide and/or nitric oxide, and eliminating these signals would result in a delay in apoptosis. Additionally, most cells treated with exogenous mature IL-1β do not die, suggesting that ICE-family activation, leading to the processing of additional substrates, is a prerequisite for cell death. Clearly, mature IL-1β can not activate the ICE-family, a characteristic which it differs from TNF-α. However, under conditions where cells are properly primed, mature IL-1β alone induces cell death, even in the absence of ICE activity as demonstrated by apoptosis induced by mature IL-1β in $G_1$/S phase arrested HeLa/CrmA cells. In addition, ICH-1$_L$ appears to become activated in COS cells upon exposure to mature IL-1β or TNF-α. Surprisingly, ICH-1$_L$ induces cell death sensitive to IL-1Ra when coexpressed with proIL-1β, indicating that ICH-1$_L$ either itself or through another ICE-like protease processes proIL-1β when both are present in high concentrations.

In view of the above results which point to a definite role of ICE in apoptosis, it is interesting that ICE knock-out mice are developmentally normal (Li, P., et al., *Cell* 80:401–411 (1995); Kuida, K., et al., *Science* 267:2000–2002 (1995)). To date, the only resistance to apoptosis reported in this mouse is in anti-Fas mediated thymocyte cell death (Kuida, K., et al., *Science* 267:2000–2002 (1995)). It is not surprising, however, that knocking out only a single member of the ever-growing number of ICE-ced-3 homologies would not produce a striking apoptotic phenotype, considering the redundancy of such an important and terminal process such as cellular suicide.

IL-1β may also be involved in-vivo in the induction of apoptosis in virally infected cells. Several viruses have been identified which express suppressers of either IL-1β and/or of TNF-α activity. Examples other than the cowpox CrmA gene is a TNF-α binding protein expressed by the pox viruses (Smith, C. A., et al., *Science* 248: 1019 (1990)). The vaccinia and cowpox viruses express a secreted IL-1β binding protein (Spriggs, M. K., et al., *Cell* 71: 145 (1992); Alcami & Smith, *Cell* 71: 153 (1992)). These viral proteins have been shown to down modulate the immune response, and their deletion diminishes virulence. In addition to immune regulatory effects, these modulators may inhibit apoptosis in infected cells by eliminating the IL-1β and/or TNF-α signal and thereby allowing the virus to use the cellular machinery for its replication prior to cellular death. This also suggests a possible mechanism for virally mediated oncogenic transformation through the inhibition apoptosis. Knowing such a mechanism can then lead to methods for killing the oncogenically transformed cells.

Additional relevancy of the present results is that elevated levels of IL-1β message have been detected in rat models of cerebral ischemia (Lui, T., et al., *Stroke* 24: 1746 (1993); Buttini, M., et al., *Molec. Brain. Res.* 23: 126 (1994)). A separate rat model demonstrated that IL-1Ra reduces cerebral infarct size by 50% following ischemia (Relton & Rothwell, *Brain Res. Bull.* 29: 243 (1992)). In addition, brains of patients with Alzheimer's disease and Down syndrome have elevated levels of IL-1β (Sue, W., et al., *Proc. Natl. Acad. Sci. U.S.A.* 86: 7611 (1989)). These findings suggest that mature IL-1β is involved in mediating the neuronal cell death pathway under ischemic conditions, and in neurodegenerative diseases. This might be analogous to the notion that a cell needs to be "primed" (in neurons with trophic factor deprivation, in HeLa cells with hypoxia or $G_1/S$ phase arrest, and in L929 cells with TNF-α or with IL-1β) in order for mature IL-1β to activate the cell death program. In-vivo, the "primed" cell idea may translate to an ill cell which is a burden to the organism, and in an example of cellular altruism, the ICE pathway is activated, leading to the production of mature IL-1β and culminating in cellular suicide. Mature IL-1β plays a pivotal role in cellular homeostasis. It both modulates the apoptotic cascade and activates the immune system; processes which are respectively involved in the execution and elimination of unwanted cells.

CONCLUSION

The interleukin-1β converting enzyme (ICE) family plays an important role in regulating vertebrate cell death. To date, no substrate of any apoptosis inducing gene has been identified which mediates cell death. ProIL-1β is the only known physiologic substrate of ICE.

A dual functional role for mature IL-1β in ICE mediated apoptosis was established. It was found that when produced endogenously (i.e., following ICE activation) IL-1β mediates cell death, but when provided exogenously IL-1β can either stimulate or inhibit cell death. In addition, mature IL-1β itself induces cell death through a pathway independent of CrmA-sensitive gene activity, and it cooperates with ICE and ICH-$1_L$ in apoptosis.

It was further demonstrated that if IL-1β bound to its receptor before exposure to an apoptotic stimulus, it inhibited programmed cell death (by down-regulating the IL-1β receptor); in contrast, if IL-1β bound after ICE was activated it enhanced cell death. IL-1 receptor antagonist (IL-1Ra) inhibits apoptosis induced by trophic factor deprivation in primary neurons, and by hypoxia or TNF-α in fibroblasts.

In addition, it was demonstrated that Ice required the co-expression of pro-IL-1β to induce apoptosis in COS cells. Cell death was inhibited by blocking IL-1β from binding to its receptor, indicating that following ICE activation, COS cells required IL-1β signal transduction for the completion of the suicide program. The results demonstrated that endogenously produced mature IL-1β plays in integral role in ICE mediated apoptosis. Thus, 1) IL-1β had anti-apoptotic activity when added exogenously prior to exposure to apoptotic stimuli, which was in part due to IL-1 receptor downregulation, 2) ICE cleavage of pro-IL-1β was an important step in apoptosis and 3) mature IL-1β may function as a positive or negative mediator of cell death.

These findings identify proIL-1β as the first substrate of any apoptosis inducing gene, whose cleavage product is a downstream mediator of the apoptotic cascade, and provides further evidence for a role of ICE in apoptosis.

All references mentioned herein are incorporated by reference in the disclosure. Having now fully described the invention by way of illustration and example for purposes of clarity and understanding, it will be apparent to those of ordinary skill in the art that certain changes and modification may be made in the disclosed embodiments and such modification are intended to be within the scope of the present invention. As examples, the preferred embodiments constitute only one form of carrying out the claimed invention.

What is claimed is:

1. A method for inhibiting programmed cell death (apoptosis), said method comprising:
    (a) providing to a cell or cells an agent that blocks interleukin-1β (IL-1β) receptor binding and
    (b) inhibiting programmed cell death.

2. The method of claim 1, wherein said agent is selected from the group consisting of IL-1RA, an anti-IL-1 polyclonal neutralizing antibody and anti-IL-1 type 1 receptor neutralizing polyclonal antibody.

3. The method of claim 1, wherein said cell is a vertebrate cell.

4. The method of claim 3, wherein said vertebrate cell is a mammalian cell.

5. The method of claim 1, wherein said agent that blocks IL-1β receptor binding is IL-1Ra.

6. The method of claim 5, wherein said cell is a vertebrate cell.

7. The method of claim 6, wherein said vertebrate cell is a mammalian cell.

8. The method of claim 1, wherein said agent that blocks IL-1β receptor binding is an anti-IL1 polyclonal neutralizing antibody.

9. The method of claim 1, wherein said agent that blocks IL-1β receptor binding is an anti-IL-1 type-1 receptor neutralizing polyclonal antibody.

* * * * *